United States Patent
Peters et al.

(10) Patent No.: US 9,606,122 B2
(45) Date of Patent: *Mar. 28, 2017

(54) PROGNOSIS OF OESOPHAGEAL AND GASTRO-OESOPHAGEAL JUNCTIONAL CANCER

(75) Inventors: Christopher J. Peters, Swindon (GB); Carlos Caldas, Swindon (PT); Rebecca C. Fitzgerald, Swindon (GB)

(73) Assignees: Cambridge Enterprise Limited, Cambridge (GB); Medical Research Council, Swindon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/636,958

(22) PCT Filed: Mar. 24, 2011

(86) PCT No.: PCT/GB2011/000424
§ 371 (c)(1),
(2), (4) Date: Sep. 24, 2012

(87) PCT Pub. No.: WO2011/117586
PCT Pub. Date: Sep. 29, 2011

(65) Prior Publication Data
US 2013/0065785 A1 Mar. 14, 2013

(30) Foreign Application Priority Data
Mar. 24, 2010 (GB) .................... 1005048.2

(51) Int. Cl.
*C12Q 1/68* (2006.01)
*G01N 33/574* (2006.01)

(52) U.S. Cl.
CPC . *G01N 33/57407* (2013.01); *G01N 33/57484* (2013.01)

(58) Field of Classification Search
CPC ............... G01N 33/57484; G01N 33/57407
See application file for complete search history.

(56) References Cited

U.S. PATENT DOCUMENTS

2006/0019256 A1* 1/2006 Clarke et al. .................. 435/6
2007/0099209 A1* 5/2007 Clarke et al. .................. 435/6

FOREIGN PATENT DOCUMENTS

| GB | WO 2007074341 A1 * | 7/2007 | ........... C12Q 1/6886 |
|---|---|---|---|
| JP | 2009039052 | 2/2009 | |
| WO | 01/74405 | 10/2001 | |
| WO | 2007/074341 | 7/2007 | |

OTHER PUBLICATIONS

Wang et al. (2007) SIRT2 deacetylates FOXO3a in response to oxidative stress and caloric restriction. Aging Cell, 6:505-514.*
Urano et al. (2009) TRIM44 interacts with and stabilizes terf, a TRIM ubiquitin E3 ligase. Biochemical and Biophysical Research Communications, 383:263-268.*
Hammoud et al. (2008) Differential gene expression profiling of esophageal adenocarcinoma. The Journal of Thoracic and Cardiovascular Surgery, 137(4):829-834.*
Whitehead et al. (2005) Variation in tissue-specific gene expression among natural populations. Genome Biology, 6:R13, 14 pages.*
Greenawalt et al. (2007) Gene expression profiling of esophageal cancer: Comparative analysis of Barrett's esophagus, adenocarcinoma, and squamous cell carcinoma. International Journal of Cancer, 120:1914-1921.*
Excerpt from supplementary Table 3 from Greenawalt et al. (2007) International Journal of Cancer, 120:1914-1921; obtained from <http://onlinelibrary.wiley.com/doi/10.1002/ijc.22501/suppinfo> on Sep. 2, 2014, 1 page.*
Wang et al. (2007) Expression of Epidermal Growth Factor Receptor in Esophageal and Esophagogastric Junction Adenocarcinomas. Cancer, 109(4):658-667.*
Q96DX7.1 (TRIM44 UniProtKB/Swiss-Prot Accession, GI 56404940, priority to Mar. 2, 2010, 3 pages).*
Q8IXJ6.2 (SIRT2 UniProtKB/Swiss-Prot Accession, GI 38258608, priority to Dec. 15, 2009, 10 pages).*
NM_005228 (EGFR NCBI Reference Sequence, GI 41327737, priority to Mar. 5, 2010, 6 pages).*
NM_000378.3 (WT1 NCBI Reference Sequence, GI 65507713, priority to Mar. 4, 2010, 6 pages).*
NM_017583.4 (TRIM44 NCBI Reference Sequence, GI:205277436, priority to Feb. 7, 2010, 4 pages).*
NM_012237.2 (SIRT2 NCBI Reference Sequence, GI:13775599, priority to Jan. 31, 2010, 5 pages).*
Buck et al. (1999) Design Strategies and Performance of Custom DNA Sequencing Primers. Biotechniques, 27(3): 528-536.*
Rozen et al. (2000) Primer3 on the WWW for general users and for biologist programmers. In: Krawetz S, Misener S (eds) Bioinformatics Methods and Protocols: Methods in Molecular Biology. Humana Press, Totowa, NJ, pp. 365-389.*
Joshi et al. (2005) High Gene Expression of TS1, GSTP1, and ERCC1 Are Risk Factors for Survival in Patients Treated with Trimodality Therapy for Esophageal Cancer. Clinical Cancer Research, 11:2215-2221.*

(Continued)

*Primary Examiner* — Neil P Hammell
(74) *Attorney, Agent, or Firm* — Wiley Rein LLP

(57) ABSTRACT

The present invention relates to a method of aiding in the prognosis of a subject with oesophageal and/or gastro-oesophageal junctional (GOJ) adenocarcinoma, the method comprising the steps of: (a) providing a sample from the subject, (b) determining the expression level of biomarkers TRIM44 and SIRT2 in said sample, and either (i) determining the expression level of biomarker PAPPS2 in said sample; or (ii) determining the expression level of biomarkers WT1 and EGFR in said sample; (c) comparing the expression level of each of said biomarkers to a corresponding reference standard, (d) determining the biomarkers of (b) whose expression is dysregulated compared to the reference standard, (e) inferring from the dysregulated biomarkers identified in (d) the prognosis of 5-year survival, wherein the greater the number of said biomarkers which are dysregulated, the greater the reduction in prognosis of 5-year survival. The invention also relates to kits, uses and devices.

4 Claims, 11 Drawing Sheets

(56) References Cited

OTHER PUBLICATIONS

Peters et al., Gut, 59(4):A31 (2009). "Generation and validation of a prognostic gene signature for oesophageal adenocarcinoma."

Oji et al., Retrieved from the Internet, pp. 712-717 (Aug. 1, 2003). "Overexpression of the Wilms' tumor gene WT1 in colorectal adenocarcinoma." URL: http://onlinelibrary.wiley.com/store/10.1111/j.1349-7006.2003.tb01507.x/asset/j.1349-7006.2003.tb01507.x.pdf?v=1&t=gpjo6pyt&s=e875132549ce140e22693286714e69935c393aaf.

Peters et al., Gut, 59(4-1)A24-A27 (2010). "A clinically applicable three gene signature is independently highly prognostic in oesophageal and junctional adenocarcinoma."

Peters, C.J., Gastroenterology, 139(6):1995-2004 (2010). "A 4-gene signature predicts survival of patients with resected adenocarcinoma of the esophagus, junction, and gastric cardia."

Greenawalt et al., Int J Cancer, 120:1914-1921 (2007). "Gene expression profiling of esophageal cancer: Comparative analysis of Barrett's esophagus, adenocarcinoma, and squamos cell carcinoma."

\* cited by examiner

PROGNOSIS OF OESOPHAGEAL AND GASTRO-OESOPHAGEAL JUNCTIONAL CANCER

SEQUENCE LISTING

The instant application contains a Sequence Listing which has been submitted in ASCII format via EFS-Web and is hereby incorporated by reference in its entirety. Said ASCII copy, created on Nov. 13, 2012, is named 20121114_SequenceListing-TextFile_065986_012000_US and is 3,359 bytes in size.

FIELD OF THE INVENTION

The present invention relates to the provision of a practical and reliable method or kit to aid in the prognosis of oesophageal and gastro-oesophageal junctional (GOJ) adenocarcinoma.

BACKGROUND TO THE INVENTION

The incidence of oesophageal and gastro-oesophageal junctional (GOJ) adenocarcinoma has increased 6 fold in the last 30 years, making to it the commonest esophageal malignancy in the western world[1]. Unfortunately five year survival remains less than 8% for all patients diagnosed[1] and only 18-23% for patients undergoing surgery[2]. It is staged using the internationally recognized TNM system[3], although this has limited ability to stratify patients according to their likely outcome. While patients with advanced stage tumors clearly do worse than those with earlier disease, most patients present late (T3N1) and even within this group there are wide variations in survival. The highly invasive nature of esophageal surgery and the toxic nature of neoadjuvant regimes make it important to find better ways to select treatment. Complex management decisions require more accurate prognostic information. In other epithelial tumors molecular signatures have proven to be prognostic. In breast cancer gene signatures have been shown to predict survival[4,5] and response to chemotherapy[6] with good external validation[7,8]. In general whilst the breast cancer prognostic signatures have been well validated the same is not true of most molecular predictors of outcome. No molecular signatures have been incorporated into formal TNM staging, though some have gained a place in national cancer guidelines[9]. It has been proposed that a biomarker of prognosis should be sensitive, specific, cost effective, fast, robust against variability and better than current clinical parameters[10]. The US FDA and National Institute of Standards and Technology (NIST) have proposed five steps of biomarker validation; preclinical exploration, clinical assay and validation, retrospective longitudinal validation, prospective validation and demonstration of benefits in cancer outcomes[11,12]. Other reviews looking at predictors of outcome have reiterated the need for external validation and the development of a test that has general clinical applicability[13-16], whilst the REMARK guidelines suggested the requirements for reporting prognostic biomarker studies[17].

While work continues to better stratify oesophageal and GOJ adenocarcinomas by more detailed characterization of clinical and pathological features[18-20], there remains a need in the art to prepare a robust and practical method and kit to aid in the prognosis of oesophageal and GOJ adenocarcinomas.

SUMMARY OF THE INVENTION

In one aspect the invention relates to a method of aiding in the prognosis of a subject with oesophageal and/or gastro-oesophageal junctional (GOJ) adenocarcinoma, the method comprising the steps of:
(a) providing a sample from the subject,
(b) determining the expression level of biomarkers TRIM44 and SIRT2 in said sample, and either
  (i) determining the expression level of biomarker PAPPS2 in said sample; or
  (ii) determining the expression level of biomarkers WT1 and EGFR in said sample;
(c) comparing the expression level of each of said biomarkers to a corresponding reference standard,
(d) determining the biomarkers of (b) whose expression is dysregulated compared to the reference standard,
(e) inferring from the dysregulated biomarkers identified in (d) the prognosis of 5-year survival, wherein the greater the number of said biomarkers which are dysregulated, the greater the reduction in prognosis of 5-year survival.

In another aspect, the invention relates to a method as described above, wherein step (b) further comprises determining the expression level of biomarker DCK.

In another aspect, the invention relates to a method as described above, wherein step (b) comprises determining the expression level of each of TRIM44 and SIRT2 and PAPPS2 and DCK. This combination of markers has the advantage of providing a very simple readout. Each of these markers provides a binary readout.

In another aspect, the invention relates to a method as described above, wherein step (b) comprises determining the expression level of each of TRIM44 and SIRT2 and WT1 and EGFR. This combination of markers has the advantage of providing a robust separation of patients into each of the 4 main prognostic outcomes. In addition this combination of markers lends itself to statistical analysis. This combination of markers can be advantageous to use in inferring survival time.

In another aspect the invention relates to a method as described above wherein step (b) comprises determining the expression level of each of TRIM44 and SIRT2 and PAPPS2 and WT1 and EGFR. This has the advantage of combining the most informative markers into a single readout.

In another aspect the invention relates to a method as described above wherein step (b) further comprises determining the expression level of biomarker MTMR9.

In another aspect the invention relates to a method as described above wherein step (b) further comprises determining the expression level of biomarker NEIL2.

In another aspect the invention relates to a method as described above wherein step (b) comprises determining the expression level of each of TRIM44 and SIRT2 and PAPPS2 and WT1 and EGFR and DCK and MTMR9 and NEIL2.

Suitably the expression level of the biomarkers is determined by measuring the quantity of protein present.

Suitably the determination is done by immunohistochemistry.

Suitably the biological sample from the subject comprises tumour tissue.

In another aspect, the invention relates to a kit comprising reagents for determining the expression level of each of the biomarkers as defined in any of the methods described above in a biological sample.

In another aspect, the invention relates to use for applications relating to prognosis of adenocarcinoma, of a material which recognises, binds to or has affinity for certain polypeptides, or a fragment, variant or mutant thereof, wherein the polypeptides are as defined in any of the methods described above. Suitably said use is use of a combination of materials, each of which respectively recognises, binds to or has affinity for one or more of said polypeptide(s), or a fragment, variant or mutant thereof.

In another aspect, the invention relates to an assay device for use in the prognosis of adenocarcinoma, which comprises a solid substrate having a location containing a material, which recognises, binds to or has affinity for certain polypeptides, or a fragment, variant or mutant thereof, wherein the polypeptides are as defined in any of the methods described above.

The invention also relates to a method of aiding in the prognosis of a subject with oesophageal and/or gastro-oesophageal junctional (GOJ) adenocarcinoma, the method comprising the steps of:
 (a) providing a sample from the subject,
 (b) determining the expression level of biomarkers TRIM44, PAPSS2 and SIRT2 in said sample,
 (c) comparing the expression level of each of said biomarkers to a corresponding reference standard,
 (d) determining the number of biomarkers of (b) whose expression is dysregulated compared to the reference standard,
 (e) wherein the greater the number of said biomarkers which are dysregulated, the greater the reduction in prognosis of 5-year survival.

Suitably the group of biomarkers of (b) further comprises biomarker DCK.

Suitably if none of the four biomarkers is dysregulated, then the prognosis is a 58% probability that the subject will survive for more than 5 years.

Suitably the expression level of the biomarkers is determined by measuring the quantity of protein present. Suitably the determination is done by immunohistochemistry.

Suitably the expression level of the biomarkers is determined by the quantity of RNA present. Suitably the determination is done by RT-PCR.

Suitably the primers used are selected from the group consisting of SEQ. ID. NO.s 1-16.

Suitably the method further comprises determining the expression level of one or more biomarkers selected from the group consisting of ADCY9, C5AR1, UBE2D2, MNT, PLK1 and NEU4.

Suitably the method further comprises determining the expression level of one or more biomarkers selected from the group consisting of NEDD9(HEF1), UNC93B1, LPHN3, EFCBP1, TSPAN5, TREM2, ITGB6, ARTS-1, TCF15 and FGD2.

Suitably the biological sample from the subject comprises tumour tissue.

In another aspect, the invention relates to a kit comprising reagents for determining the expression level of biomarkers TRIM44, PAPSS2 and SIRT2 in a biological sample. Suitably the kit further comprises reagents for determining the expression level of biomarker DCK in a biological sample. Suitably the kit further comprises reagents for determining the expression level of at least one biomarker selected from the group consisting of ADCY9, C5AR1, UBE2D2, MNT, PLK1 and NEU4. Suitably the kit further comprises reagents for determining the expression level of at least one biomarker selected from the group consisting of NEDD9 (HEF1), UNC93B1, LPHN3, EFCBP1, TSPAN5, TREM2, ITGB6, ARTS-1, TCF15 and FGD2.

In another aspect, the invention relates to use for applications relating to prognosis of adenocarcinoma, of a material which recognises, binds to or has affinity for a polypeptide, or a fragment, variant or mutant thereof, wherein the polypeptide is selected from TRIM44, PAPSS2, SIRT2 and DCK.

In another aspect, the invention relates to use as described above of a combination of materials, each of which respectively recognises, binds to or has affinity for one or more of said polypeptide(s), or a fragment, variant or mutant thereof. Suitably the or each material is an antibody or antibody chip. Suitably the material is an antibody with specificity for one or more of said polypeptide(s), or a fragment, variant or mutant thereof.

In another aspect, the invention relates to an assay device for use in the prognosis of adenocarcinoma, which comprises a solid substrate having a location containing a material, which recognises, binds to or has affinity for a polypeptide, or a fragment, variant or mutant thereof, wherein the polypeptide is selected from TRIM44, PAPSS2, SIRT2 and DCK.

Suitably the solid substrate has a plurality of locations each respectively containing a material which recognises, binds to or has affinity for a polypeptide, or a fragment, variant or mutant thereof, wherein the polypeptide is selected from TRIM44, PAPSS2, SIRT2 and DCK. Suitably the material is an antibody or antibody chip.

Suitably the assay device as described above has a unique addressable location for each antibody, thereby to permit an assay readout for each individual polypeptide or for any combination of polypeptides.

Suitably the assay device as described above includes an antibody to a polypeptide wherein the polypeptide is selected from TRIM44, PAPSS2, SIRT2 and DCK.

In another aspect, the invention relates to a kit for use in the prognosis of adenocarcinoma, comprising an assay device as described above, and means for detecting the amount of one or more of the polypeptides in a sample taken from a subject.

In another aspect, the invention relates to a kit for use in the prognosis of adenocarcinoma, said kit comprising one or more primers selected from the group consisting of SEQ. ID. NO.s 1-16.

In another aspect, the invention relates to a method of providing a prognosis of 5-year survival in a subject with oesophageal and/or gastro-oesophageal junctional (GOJ) adenocarcinoma, the method comprising the steps of:
 (a) providing a biological sample from the subject,
 (b) determining the expression level of biomarker TRIM44 in said sample,
 (c) comparing the expression level of said biomarker to a reference standard,
 (d) determining that if the expression of said TRIM44 biomarker is dysregulated, then the prognosis of survival is reduced. Suitably the expression level of the TRIM44 biomarker is determined by measuring the quantity of protein present. Suitably determination is done by immunohistochemistry.

DESCRIPTION OF THE DRAWINGS

The invention will now be described in relation to the drawings in which.

DETAILED DESCRIPTION OF THE INVENTION

Figure 1:
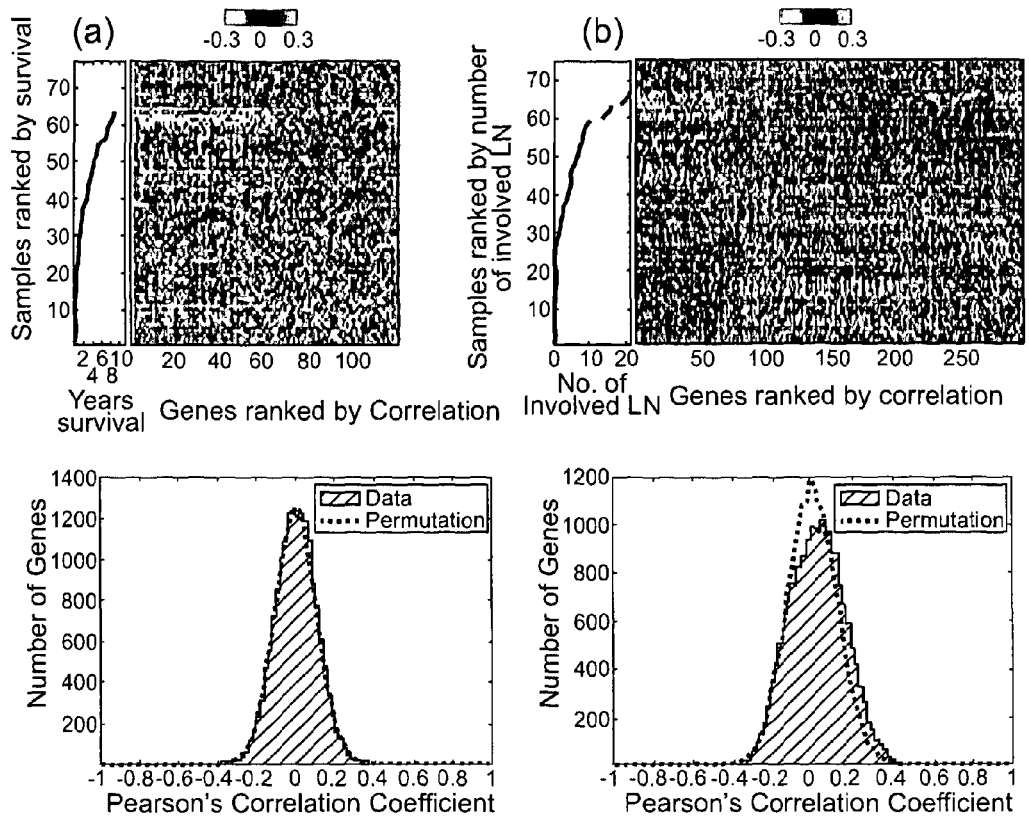
FIG. 1—Heatmaps of gene expression associated with a) survival and b) the number of involved lymph nodes with the corresponding histograms of Pearson's correlation coefficients. On the heatmaps samples are ranked on the y axis in order of a) increasing survival and b) increasing number of involved lymph nodes whilst the genes associated with this feature are ranked along the x axis. The blue bars on the histograms represent the distribution of the data and the red lines represents the distribution expected from the Monte Carlo Simulation.

The present invention regards the provision of a method or kit to aid in prognosis of oesophageal and GOJ adenocarcinomas.

It is known in the art that the prognostic result depends on many factors, all of which vary from patient to patient. Thus the prognostic outcome of the method or kit according to the invention may be combined with other tests in order to improve prognostic predictions. The present invention provides for the aiding of prognosis.

Said method or kit to aid in said prognosis relies on analysing the expression level of a specific set of biomarkers. Together these markers form a prognostic signature which advantageously aids prediction of the prognosis for the subject.

Within the context of the present invention the term biomarker should be understood to refer to a gene product such as a mRNA or a polypeptide or some other indicator of expression of the marker. The gene product may be post-translationally modified, for example glycolysated, fully folded protein or may be a polypeptide precursor or other suitable molecule. The important point is that the molecule which is assayed should be indicative of expression of the gene product and not merely the presence of the genomic nucleotide sequence which will of course be present in the majority of cells of the subject of interest regardless of its expression state. Naturally the context may provide more detail if particular embodiments are envisaged (for example the term "gene biomarker" implies a nucleic acid form of the marker such as an mRNA.) Within the context of the present invention, said biomarkers will be conventionally denoted by the name of the human protein.

The sequences of each of the biomarkers of the present invention are known in the art and have accession numbers that allow a person skilled in the art to access the relevant information. Information can be accessed from internet sites hosted by organizations such as the National Institutes of Health, National Center for Biotechnology Information.

Table 1, which is found in the annex, lists some preferred biomarkers according to the present invention with their accession numbers.

One aspect of the invention is a method of aiding a prognosis of survival in a subject with oesophageal and/or gastro-oesophageal junctional (GOJ) adenocarcinoma, the method comprising the steps of:
  (a) providing a biological sample from the subject,
  (b) determining the expression level of biomarkers TRIM44, PAPSS2 and SIRT2 in said sample,
  (c) comparing the expression level of said biomarkers to a reference standard,
  (d) determining that if the expression of at least one of said biomarkers is dysregulated, then the prognosis of survival will be reduced.

In another aspect the invention provides a method of aiding in the prognosis of a subject with oesophageal and/or gastro-oesophageal junctional (GOJ) adenocarcinoma, the method comprising the steps of:
  (a) providing a sample from the subject,
  (b) determining the expression level of biomarkers TRIM44, PAPSS2 and SIRT2 in said sample,
  (c) comparing the expression level of each of said biomarkers to a corresponding reference standard,
  (d) determining the number of biomarkers of (b) whose expression is dysregulated compared to the reference standard,
wherein the greater the number of said biomarkers which are dysregulated, the greater the reduction in prognosis of 5-year survival.

The sample is suitably any biological sample which may contain cells from the lesion such as the adenocarcinoma under investigation. The sample is suitably a biopsy. The sample is suitably a biopsy directed to the area of the tumour or to the tumour itself. Suitably the biopsy comprises tumour cells.

The invention may comprise collection of the biopsy by any suitable means.

Suitably the invention does not comprise collection of the biopsy.

Suitably the step of providing a sample from the subject comprises only in vitro procedures such as processing a biopsy e.g. thawing a biopsy or preparing protein(s) and/or nucleic acid extract(s) and/or cell lysates from a sample of material in vitro. Suitably the method of the invention is conducted in vitro and suitably does not require the presence of the subject. Suitably the method is an in vitro method.

Within the context of the present invention, a reference standard functions as an object of comparison to which the expression levels present in the sample of the subject can be compared to. The reference standard may comprise a sample from a healthy subject which is analysed in parallel with the sample of interest. Alternatively said reference standard may comprise expression level value(s) for said biomarkers previously determined from a sample taken from a healthy subject so as to give values of expression level of said biomarkers to compare with. This has the advantage of not requiring parallel analysis of the reference sample each time the method is carried out. Suitably the healthy person is an individual of similar demographic characteristics, such as age, sex, weight and any other relevant parameters, to the subject being considered.

The reference standard may also be a set of expression level values for said biomarkers determined over time as a mean. This has the advantage of eliminating the practical issues of taking and measuring a sample from a separate individual every time the method is performed. Suitably said set of expression level values for said biomarkers determined over time as a mean would be divided into different categories divided by medical characteristics, such as age, sex, weight and others, so as to provide a more directly comparable set of values for the particular subject being examined.

Within the present method, the values of expression level of said biomarkers are compared to evaluate whether their expression is dysregulated. Within the context of the present invention, a dysregulation of a biomarker's expression is when the biomarker is expressed at least 1.3 fold more or less than the reference standard, preferably at least 1.4 fold more or less, more preferably at least 1.5 fold more or less.

An advantage of using the method according to the invention is the prognostic power of said method. By applying the method according to the present invention to an external dataset for verification, it has been found that the prognostic power of the method is higher if the expression levels of all three biomarkers TRIM44, PAPSS2 and SIRT2 are determined as opposed to the determination of the expression level of only two of said biomarkers.

Suitably the method according to the invention further comprises the determination of the expression level of DCK, as this improves the prognostic power of the method. Such a method is able to identify patients that have a five-year survival rate or greater 58% of the time, which is very advantageous for oesophageal and/or gastro-oesophageal junctional (GOJ) adenocarcinoma. This exemplary figure is the prognostic outcome when none of the 4 biomarkers cited above are dysregulated.

It is also noteworthy that even patients staged T3N1 but with 0/4 TRIM44, SIRT2, PAPPS2 and DCK genes dysregulated have a five year survival of 50%. Equally the signature of dysregulation of all of the 4 TRIM44, SIRT2, PAPPS2 and DCK biomarkers identifies a population with a very poor prognosis, a five year survival of just 14%. This group (17% of the overall cohort in the examples and 22% of neoadjuvant chemotherapy treated patients) may do poorly regardless of what treatment they receive and therefore might be spared the morbidity of surgery and/or chemotherapy.

If dysregulation of any of these four biomarkers TRIM44, SIRT2, PAPPS2 and DCK, or of the other biomarkers disclosed herein, can be targeted with therapeutic agents there is the opportunity to develop a personalized treatment regime. This would aim to target the combination of pathways important for a given tumor.

Mode of Analysis

The method of determining the expression level depends on the state of the biomarker chosen.

In one preferred embodiment of the method according to the invention, the biomarkers are analysed as proteins. In such an embodiment, the determination of the expression level can be done by determining the levels of protein expressed. Protocols for measuring protein level(s) in a biological sample are well known in the art. One notable example would be the use of antibodies in immunohistochemical measurements. The advantage of said embodiment of the method according to the present invention is that immunohistochemical methods and apparatus are widely available in hospitals and can be easily performed.

In another preferred embodiment of the method according to the invention, the biomarkers are determined when in nucleic acid form. Suitably their expression level is measured when they are in RNA form. The protocols for doing that from a biological sample are well known in the art. One notable example would be the use of RT-PCR. For this, forward and reverse primers are required. Preferably said primers are chosen from the group consisting of SEQ ID NO. 1-16, as described here below in WIPO ST25 format. RT-PCR is suitably performed according to standard methods known in the art such as described in Nolan T, Hands R E, Bustin S A (2006). Quantification of mRNA using real-time RT-PCR. Nature Protocols; 1: 1559-1582, which is incorporated herein by reference specifically for the RT-PCR protocols.

Reference Sequence

When particular amino acid residues are referred to using numeric addresses, the numbering is taken using the full length amino acid sequence as the reference sequence. This is to be used as is well understood in the art to locate the residue of interest. This is not always a strict counting exercise—attention must be paid to the context. For example, if the protein of interest such as human TRIM44 is of a slightly different length, then location of the correct residue in the TRIM44 sequence corresponding to a particular residue may require the sequences to be aligned and the equivalent or corresponding residue picked, rather than simply taking the identically numbered residue of the sequence of interest. This is well within the ambit of the skilled reader.

Moreover, in the context of the present invention it is detection of particular polypeptide sequences corresponding to those described which is important. The techniques and/or reagents for such detection are widely available and/or straightforward to obtain or generate. Exemplary materials and techniques are provided in the examples section. Detection of a particular polypeptide e.g. the polypeptide product of a particular gene is suitably to be considered at the level of protein detection. It is a question of expression of the protein, rather than a determination of a specific or precise 100% identical amino acid sequence. Exemplary amino acid sequences are provided as guidance for the polypeptide being detected and are not intended to constrain the invention to the detection of only those precise full length 100% identical amino acid sequences. Thus, variants such as allelic variants; mutants such as point mutations or short additions or deletions which do not alter the fundamental identity of the polypeptide; or fragments such as splice variants, cleaved or mature proteins; post translationally modified proteins or other such common forms are to be considered within the remit of determining the expression level of the various biomarker proteins disclosed.

A fragment is suitably at least 10 amino acids in length, suitably at least 25 amino acids, suitably at least 50 amino acids, suitably at least 100 amino acids, suitably at least 200 amino acids, suitably the majority of the polypeptide of interest. Suitably a fragment comprises a whole motif or a whole domain of the polypeptide of interest.

Sequence Homology/Identity

Although sequence homology can also be considered in terms of functional similarity (i.e., amino acid residues having similar chemical properties/functions), in the context of the present document it is preferred to express homology in terms of sequence identity.

Sequence comparisons can be conducted by eye or, more usually, with the aid of readily available sequence comparison programs. These publicly and commercially available computer programs can calculate percent homology (such as percent identity) between two or more sequences.

Percent identity may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues (for example less than 50 contiguous amino acids). For comparison over longer sequences, gap scoring is used to produce an optimal alignment to accurately reflect identity levels in related sequences having insertion(s) or deletion(s) relative to one another. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package, FASTA (Altschul et al., 1990, J. Mol. Biol. 215:403-410) and the GENEWORKS suite of comparison tools.

In the context of the present document, a homologous amino acid sequence is taken to include an amino acid sequence which is at least 40, 50, 60, 70, 80 or 90% identical. Most suitably a polypeptide having at least 90% sequence identity to the biomarker of interest will be taken as indicative of the presence of that biomarker; more suitably a polypeptide which is 95% or more suitably 98% identical at the amino acid level will be taken to indicate presence of that biomarker. Suitably said comparison is made over at least the length of the polypeptide or fragment which is being assayed to determine the presence or absence of the biomarker of interest. Most suitably the comparison is made across the full length of the polypeptide of interest. The same considerations apply to nucleic acid nucleotide sequences.

Prognosis

After determining the biomarkers of whose expression is dysregulated compared to the reference standard, the methods of the invention are suitably used to infer from the dysregulated biomarkers identified, the prognosis of 5-year survival. Overall, the greater the number of said biomarkers which are dysregulated, the greater the reduction in prognosis of 5-year survival.

Optionally, more detailed prognosis may be carried out.

For example the inference step of the method may comprise calculating or referring to P-values (confidence values) determined for the particular markers used or detected. Examples are presented in Table SA8.

For example the inference step may comprise application of hazard ratios. Examples are presented in Table SA8.

For example the inference step may comprise application of a Cox Hazard Proportional Model. An exemplary model is described in the examples section.

For example the inference step may comprise preparation of, and/or comparison to, a Kaplan-Meier survival curve.

In all such examples of how the inference might be arrived at, it will be noted that a key teaching of the invention is in the empirical gene signature(s) analysed. In addition, optionally expanded gene signatures such as the larger 8-gene signature are also disclosed. The specific mathematical or statistical analysis used to go from the gene signature(s) to the prognostic inference is a matter of operator choice. In case any guidance is needed, one or more of the techniques described herein may be used. Equally a similar or equivalent statistical method may be used if desired. A key advance provided by the invention is the description of the biomarkers which provide prognostic information; the precise mode of carrying out the analytical steps may be varied according to the needs of the skilled worker.

Further Combinations

The prognostic power of the method can be further improved by further assaying expression of one or more of the biomarkers chosen from ADCY9, C5AR1, UBE2D2, MNT, PLK1 and NEU4.

The prognostic power of the method can be further improved by further assaying one or more of the biomarkers selected from NEDD9 (also known as HEF1), UNC93B1, LPHN3, EFCBP1, TSPAN5, TREM2, ITGB6, ARTS-1, TCF15 and FGD2.

Suitably the sample from the subject should comprise tumour cells such as adenocarcinoma tumour cells. Such cells may be from an oesophageal tumour and/or a GOJ tumour as appropriate.

The invention may be applied as one part of a multi-part prognostic system. For example the method of the invention may be advantageously combined with TNM staging, differentiation, resection margin status, neurovascular invasion or any other prognostic indicators for adenocarcinoma. Thus the method of the invention advantageously further comprises the step of determining one or more of the TNM stage, differentiation status, resection margin status, or neurovascular invasion status of the lesion.

This has been demonstrated in the examples by entering the exemplary four gene TRIM44, SIRT2, PAPPS2 and DCK molecular prognostic signature into a multivariable Cox regression model. In this experiment, the four gene TRIM44, SIRT2, PAPPS2 and DCK signature remained in the final model along with T and N-stage (P=0.013) demonstrating its independent prognostic power. Moreover, this demonstrates that a particularly advantageous combination method comprises the method of the invention, further comprising the steps of determining the TNM stage of the lesion.

Another aspect of the present invention is the provision of a kit for aiding in the prognosis oesophageal and GOJ adenocarcinomas. Said kit comprises reagents for determining the expression level of biomarkers TRIM44, PAPSS2 and SIRT2, (or more suitably biomarkers TRIM44, PAPSS2 SIRT2 and DCK), in a biological sample. The choice of actual reagents present in the kit would depend on the state the biomarker being tested is in and it could be either for determination of the quantity of RNA or protein biomarkers expressed. The kit could thus comprise a set of reagents for determination of the quantity of RNA or reagents for the quantity of protein biomarker or both set of reagents. The kit may further comprise instructions for the use of said kit.

If the quantity of RNA biomarkers expressed is measured, then the kit preferably contains reagents to extract and select RNA from the cell and reagents to carry out RT-PCR, such as for example the primers as mentioned above, fluorescent sensors and other reagents necessary to carry out the PCR reaction. Such reagents are already known in the art.

If the quantity of protein biomarkers expressed is measured, then the kit preferably contains reagents to extract the cell content and reagents to carry out an immunohistochemical determination. As such they will contain antibodies, preferably monoclonal, raised to recognise one of the biomarkers. Said antibodies would then be either tied to a solid phase or in liquid phase. One or more additional containers may enclose elements, such as reagents or buffers, to be used in the assay. Such kits may also contain a detection reagent that contains a reporter group suitable for direct or indirect detection of antibody binding.

The kit according to the invention may further comprise reagents for detecting biomarkers as listed above for the method and found in Table 1. The kit is preferably made for detecting the expression levels of said biomarkers in a sample of the tumour.

As seen in Example 2 below, the biomarker TRIM44 can also be used alone. Thus another aspect of the invention is a method of providing a prognosis of survival in a subject with oesophageal and/or gastro-oesophageal junctional (GOJ) adenocarcinoma, the method comprising the steps of:
(a) providing a biological sample from the subject,
(b) determining the expression level of biomarker TRIM44 in said sample,
(c) comparing the expression level of said biomarker to a reference standard,
(d) determining that if the expression of said biomarkers is dysregulated, then the prognosis of survival will be reduced.

All the preferred embodiments of the method as discussed above also apply to this embodiment of the invention.

Another aspect of the invention is a kit comprising reagents used for determining the expression level of biomarker TRIM44 in a biological sample.

All the preferred embodiments of the kit as discussed above also apply to this embodiment of the invention.

The following non-limiting examples are illustrative of the present invention:

Example 1

Generation of Molecular Prognostic Signature

Method

Following appropriate ethical approval, tumor samples were collected and snap frozen in liquid nitrogen from 91 patients undergoing potentially curative resections for oesophageal and GOJ adenocarcinoma between 1992 and 2000 at the Bristol Royal Infirmary, Bristol, UK (DA). Clinical data, including survival, were collected from review of the medical records (JRER, ethical approval LREC 04/Q2006/28). The frozen sections were cut and all primary diagnoses were confirmed by an expert gastro-intestinal pathologist (VS). RNA was extracted from 10×15 µm sections of the frozen specimen using Trizol™ according to manufactures instructions (Invitrogen, Carlsbad, Calif., USA). Amplification was performed via a very low input amplification and labeling (VLI) technique utilizing two rounds of a modified MMLV-RT-mediated reverse transcription protocol[21] or a 2× UniAmp protocol using a modification of Ambion's two-round MessageAmp II kit (Ambion, Applied Biosystems). Resulting RNA was labeled with cyanine dyes and hybridized to a custom made Agilent 44K 60-mer oligo-microarray (Agilent Technologies, Santa Clara, Calif., USA) using previous described techniques 22.23.

Following hybridization, arrays were scanned and fluorescence intensities for each probe were recorded. Ratios of transcript abundance (experimental to control) were obtained following normalization and correction of the array intensity data.

Normalization of the expression arrays was carried out by determining if array intensity of reporter probes correlated with quality control parameters such as spike-in controls, 3' bias slope, etc., especially if those reporters are C-rich, If these criteria were met the correlated reporters were used as a template. This left 75 out of 91 samples with good quality normalized data. The average expression level [log(ratio)] of all reporters in the template were calculated for each experiment to get the mean biased level of each experiment and a linear regression was performed between each gene on the array and the mean biased level across all the experiments with biased effect then subtracted. Samples which did not meet the criteria were not included in the final analysis (16 out of 91).

Gene expression data analysis was performed on the 75 samples with normalized data using Rosetta Resolver gene expression analysis software (version 6.0, Rosetta Biosoftware, Seattle, Wash.) and MATLAB software (version 7.0.4, Mathworks, Natick, Mass.).

The expression array data were correlated with outcome, and the histopathological features of the tumor, using a Pearson Correlation Coefficient and the results plotted as a histogram. The clinical data for all the samples was then randomized and the process repeated multiple times with the averaged results plotted on the same histogram (a Monte Carlo Simulation)[24]. Genes that were positively or negatively correlated with the clinical features to a greater degree than the random distribution of the Monte Carlo simulation were considered potentially significant. This identified two sets of genes, one associated directly with survival and the other associated with the number of involved lymph nodes (a feature known to be predictive of outcome and therefore a surrogate of survival[18-20]). These lists were filtered by a number of criteria to produce a short list of the targets to take forward to validation.

The 270 genes associated with the number of involved lymph nodes and the 119 genes associated with survival were filtered by selecting those that appeared on both lists (n=18) and those with a P-value of <0.0001 for their association with the clinical feature (n=33 from the number of involved lymph nodes list and n=7 from the survival list) leaving a long list of 58 targets for validation.

The Monte Carlo simulation demonstrated there was a higher probability of false positives from the survival list, thus the predominance of genes from the lymph node list. It should be noted that the genes selected as predicting the number of involved lymph nodes could also be demonstrated to predict survival (data not shown).

For each of these 58 genes tumors were scored as having relative increased, decreased or neutral expression (defined as a 1.5 fold increase or decrease in normalized ratio compared to the group average). Kaplan-Meier plots were then generated to correlate each gene with survival and a log rank Mantel-Cox test was used to compare the up and down regulated groups[7]. The groups were then assessed to determine their correlation with the number of involved lymph nodes using a Kruskal-Wallis test (the data were not normally distributed)[25]. To determine the range of expression for each of the 58 genes the variance was calculated from the raw data. Gene accession numbers were then linked to the gene symbol, and function where known. Statistical analysis was carried out using SPSS Version 15.0™ (SPSS Inc., Chicago, Il, USA) and Prism Version 3.0™ (GraphPad Software Inc., San Diego, Calif., USA). The initial 58 genes in the long list were then ranked according to a number of criteria. These included 1) being associated both with survival and the number of involved lymph nodes, 2) having a P-value $<1\times10^{-4}$ for the correlation of expression with either survival or the number of involved lymph nodes, 3) having a significant difference between groups in terms of survival or the number of involved lymph nodes (P-value <0.05) 4) having a variance of expression of >0.1, 5) having a biologically interesting role (i.e. related to the cell cycle, inflammation, differentiation, etc), and 6) having antibodies available. This created a list of 10 targets for validation at the protein level.

Results

Good quality normalized gene expression data (Gene Expression Omnibus accession number GSE19417) was generated from tumor tissue specimens for 75/91 patients (table 2). For 16/91 patients the RNA was insufficient quality or quantity for robust analysis. 62% (n=47) of patients were male with a median age of 67 years (range 35-81). 47% of patients had oesophageal or Siewert type I tumors (n=36), 11% had junctional or Siewert type II tumors (n=8), and 25% had tumors in the Cardia or Siewert type III (n=12). The Siewert classification was not known for 25% of patients (n=19) but this group did not otherwise significantly differ in demographics from the patients where Siewert classification was known (data not shown). 95% of patients (n=71) were chemotherapy naïve in keeping with the historical nature of this cohort. The median follow up for all patients was 20 months (range 0.5-137), though this increased to 89 months for survivors. There was no evidence of a difference between the demographics of the 75 patients for whom normalized expression data was obtained and the 16 patients for whom there was no useable expression data.

Pearson's correlation followed by a Monte Carlo simulation identified 119 genes that were associated with survival and 270 genes that were associated with the number of involved lymph nodes, a pathological feature known to be prognostic (FIG. 1). These genes were filtered by several criteria as described above, resulting in a list of 10 for validation.

Example 2

Validation of Molecular Prognostic Signature Via Immunohistochemistry

Method

Specificity of all antibodies was confirmed by western blotting which included both positive and negative controls.

Antibodies were then optimized with positive control cell blocks and esophageal tissue prior to application to the tissue microarrays. All immunohistochemistry was carried out using the Bond™ System (Leica Microsystems (UK) Ltd, Milton Keynes, UK) according to manufactures recommendations (CJP and C-AJO, for antibody sources and immunohistochemistry conditions see table 3).

Internal validation aimed to determine if the genes identified from the expression array study were prognostic at the protein level in the generation dataset. This was carried out using tissue microarrays (TMAs) constructed from the formalin fixed paraffin embedded tissue derived from the original Bristol cohort (VS) described in Example 1. 45/75 cases had formalin fixed tissue available from the archive, triplicate cores were included from each case.

External validation aimed to prove that the signature TRIM44, SIRT2, PAPPS2 and DCK derived in the first part of the study was prognostic in an independent cohort of oesophageal and GOJ adenocarcinomas. H&E slides and the corresponding blocks were obtained for 371 patients who underwent potentially curative surgery at one of the five OCCAMS centers contributing to this project (ethical approval MREC 07/H0305/52, see acknowledgements). The TMAs were constructed in triplicate in the same way as the internal validation dataset with all original diagnoses (which are verified by 2 histopathologists in the host institution, confirmed by a further expert gastro-intestinal histopathologist (VS, MD, DR)).

Comparisons between groups were made using the $\chi^2$ test and the Mann-Whitney U test. Loss of some cores during cutting and staining of the TMA means the number of cases analysed did not reach the maximum of 45 internal and the 371 external validation patients represented in total on the arrays for each antibody.

The external validation dataset consisted of 371 cases from five OCCAMS centers. These samples were collected between 1994 and 2006 and thus included a larger proportion of neoadjuvant chemotherapy treated patients than the generation dataset in line with current clinical practice (39% versus 5%, $\chi^2$=81.41, d.f.=2, P<0.0001). The median age of patients and TNM stage were similar to the generation dataset though significantly more patients in the validation dataset were male (80% versus 62%, $\chi^2$=9.07, d.f.=1, P=0.0026) and there was a higher proportion of Siewert Type I tumors (70% versus 47%, ($\chi^2$=24.3, d.f.=3, P<0.0001). The Siewert classification was not known for 4% of tumors (n=13) but this group did not otherwise significantly differ from the patients where Siewert classification was known (data not shown). Median follow up for all patients was 17 months (range 0.5-193), similar to the generation dataset, and this rose to 57 months for survivors, which was shorter than that in the generation dataset (U=282, P=0.001) again reflecting the more contemporary nature of this cohort.

The staining of each core on the TMA was scored from 0-3 by one of two researchers blinded to outcome (CJP and C-AJO). Samples were then characterized as having over expression (score 2-3) or under expression (score 0-1) of the target. The aim was to develop a signature which could be applied robustly in a binary way for each target (positive or negative), rather than one which used a quantitative component requiring greater standardization of techniques. These categories were then compared with survival using Kaplan-Meier plots and a log rank Mantel-Cox test. A backwards stepwise Cox regression model (entry probability 0.05, removal probability 0.10) was used for Multivariable analysis.

Figure 2:
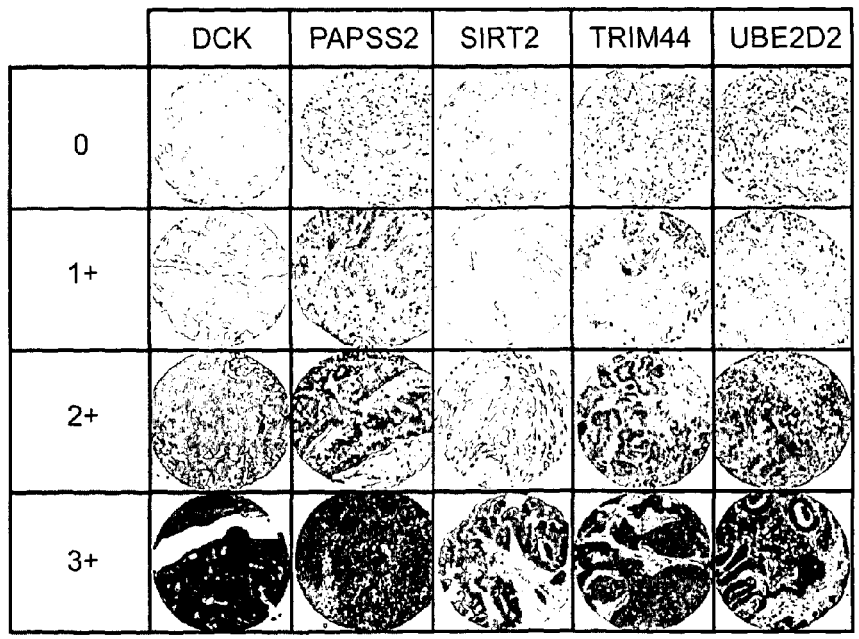
FIG. 2—Examples 0, 1+, 2+ and 3+ scoring from immunohistochemistry staining of TMAs for DCK, PAPSS2, SIRT2, and TRIM44.
Figure 3:
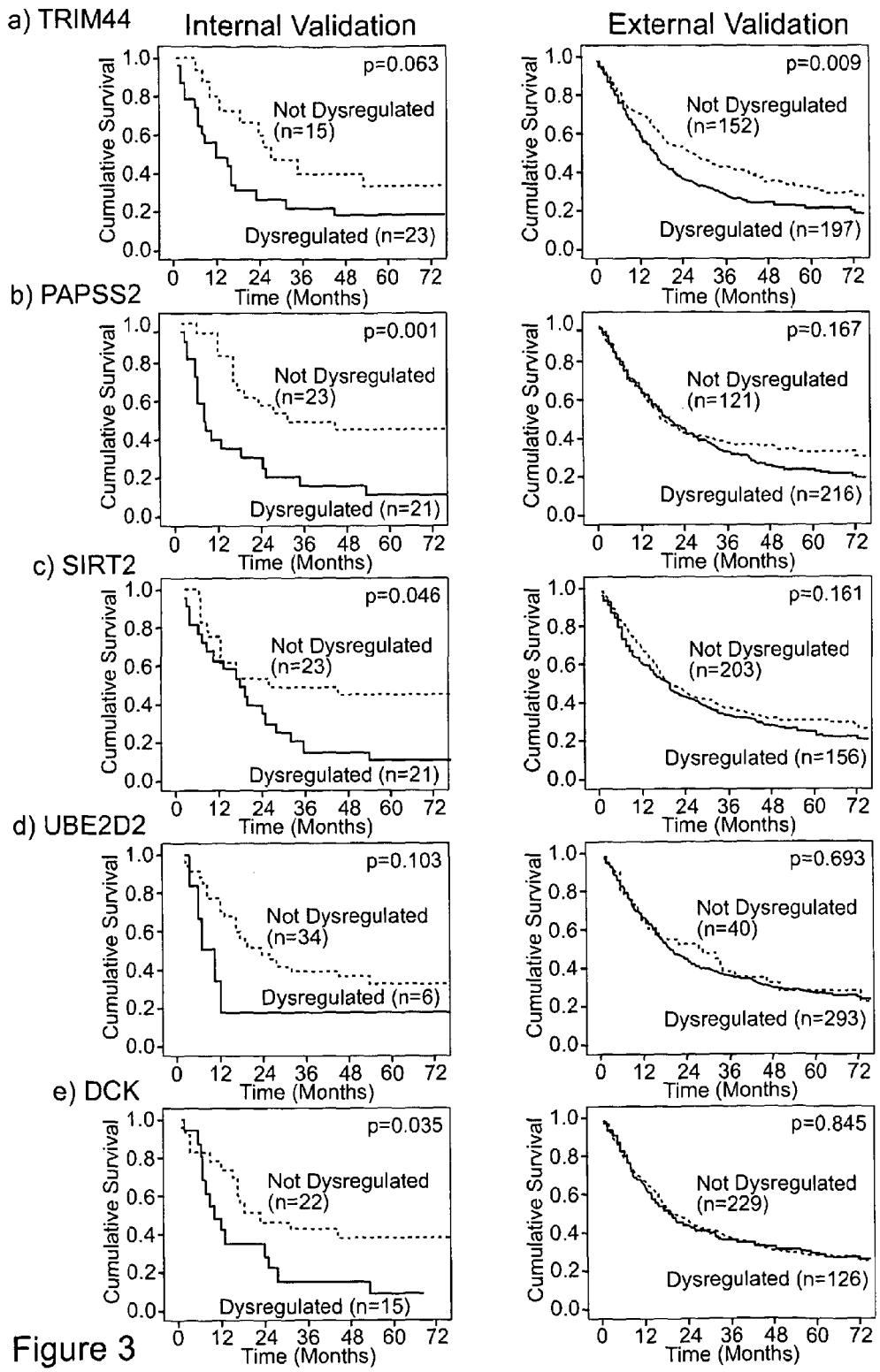
FIG. 3—Kaplan-Meier plots of survival comparing internal validation patients with dysregulation and no dysregulation of a) DCK ($\chi^2_{LR}$=4.46, 1 d.f., P=0.035), b) PAPSS2 ($\chi^2_{LR}$=12.11, 1 d.f., P=0.001), c) SIRT2 ($\chi^2_{LR}$=3.97, 1 d.f., P=0.046), and d) TRIM44 ($\chi^2_{LR}$=3.35, 1 d.f., P=0.063). Crosses represents censored data, P-values calculated using the log rank (Mantel-Cox) test).

Results 10 targets were taken forward to immunohistochemistry validation from Example 1. ADCY9 and NEU4 antibodies could not be optimized for immunohistochemistry. C5AR1, PLK-1, MNT and UBE2D2 antibodies were successfully optimized to stain tissue but showed no evidence of prognosis in the internal validation dataset. DCK, PAPSS2, SIRT2, and TRIM44 were successfully optimized to stain tissue (FIG. 2) and were prognostic in the internal validation dataset with this reaching significance for DCK ($\chi^2_{LR}$=4.46, 1 d.f., P=0.035), PAPSS2 ($\chi^2_{LR}$=12.11, 1 d.f., P=0.001) and SIRT2 ($\chi^2_{LR}$=3.97, 1 d.f., P=0.046) and borderline significance for TRIM44 ($\chi^2_{LR}$=3.35, 1 d.f., P=0.063) (table 4 and FIG. 3a-d). The four genes with evidence of prognostic power at the protein level were taken forward to the external validation dataset.

Figure 4:
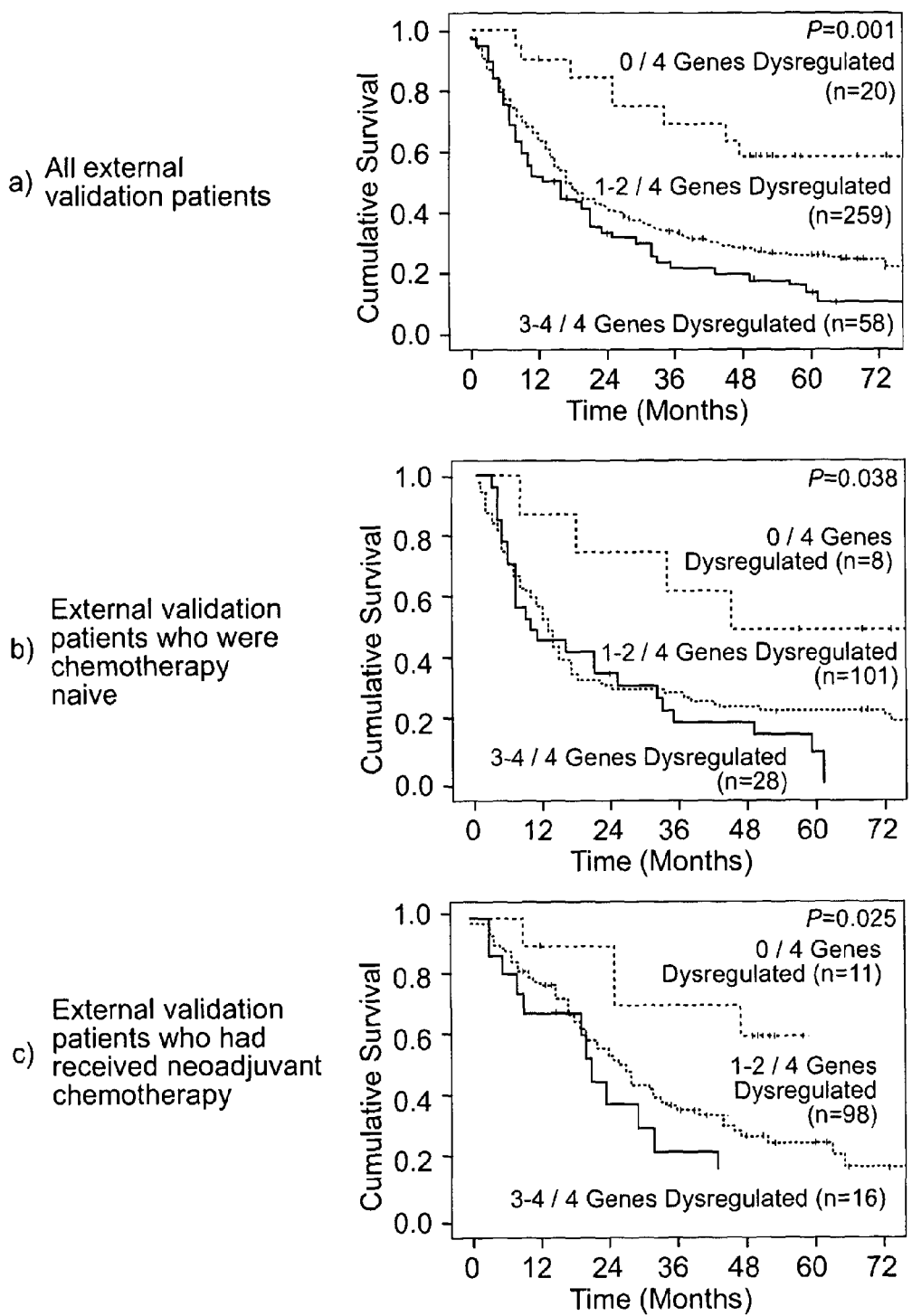
FIG. 4—Kaplan-Meier plots of survival comparing outcomes for patients with none of the four genes dysregulated and those with any of the four genes dysregulated for a) the complete external validation dataset ($\chi^2$LR=10.33, 1 d.f., p=0.001), b) external validation set patients who were chemotherapy naïve ($\chi^2$LR=4.31, 1 d.f., p=0.038), and c) external validation set patients who had received neoadjuvant chemotherapy ($\chi^2_{LR}$=4.55, 1 d.f., p=0.033). Crosses represents censored data, p-values calculated using the log rank (Mantel-Cox) test.

When the four gene molecular prognostic signature TRIM44, SIRT2, PAPPS2 and DCK was applied to the external validation dataset the number of genes dysregulated proved to be prognostic (FIG. 4a, $\chi^2_{LR}$=13.582, 2 d.f., P=0.001). Patients with none of the four genes dysregulated (five year survival 58% (95% CI 36-80%) did better than those with 1-2/4 genes dysregulated (five year survival 26% (95% CI 20-32%) who in turn did better than those with 3-4/4 genes dysregulated (five year survival 14% (95% CI 4-24%). When patients were stratified according to whether or not they had received neoadjuvant chemotherapy (n.b. this data was available for 283/371 patients), the molecular prognostic signature TRIM44, SIRT2, PAPPS2 and DCK still had excellent prognostic power in both groups (for chemotherapy naïve patients, $\chi^2_{LR}$=4.323, 2 d.f., P=0.038 and for patients who had received neoadjuvant chemotherapy $\chi^2_{LR}$=5.013, 2 d.f., P=0.025, FIG. 4b-c). Furthermore the signature TRIM44, SIRT2, PAPPS2 and DCK was able to predict outcome in Siewert Type I ($\chi^2_{LR}$=4.578, 2 d.f., P=0.032), II ($\chi^2_{LR}$=7.281, 2 d.f., P=0.007), and III tumors ($\chi^2_{LR}$=4.637, 2 d.f., P=0.031) when analyzed separately.

Figure 5:
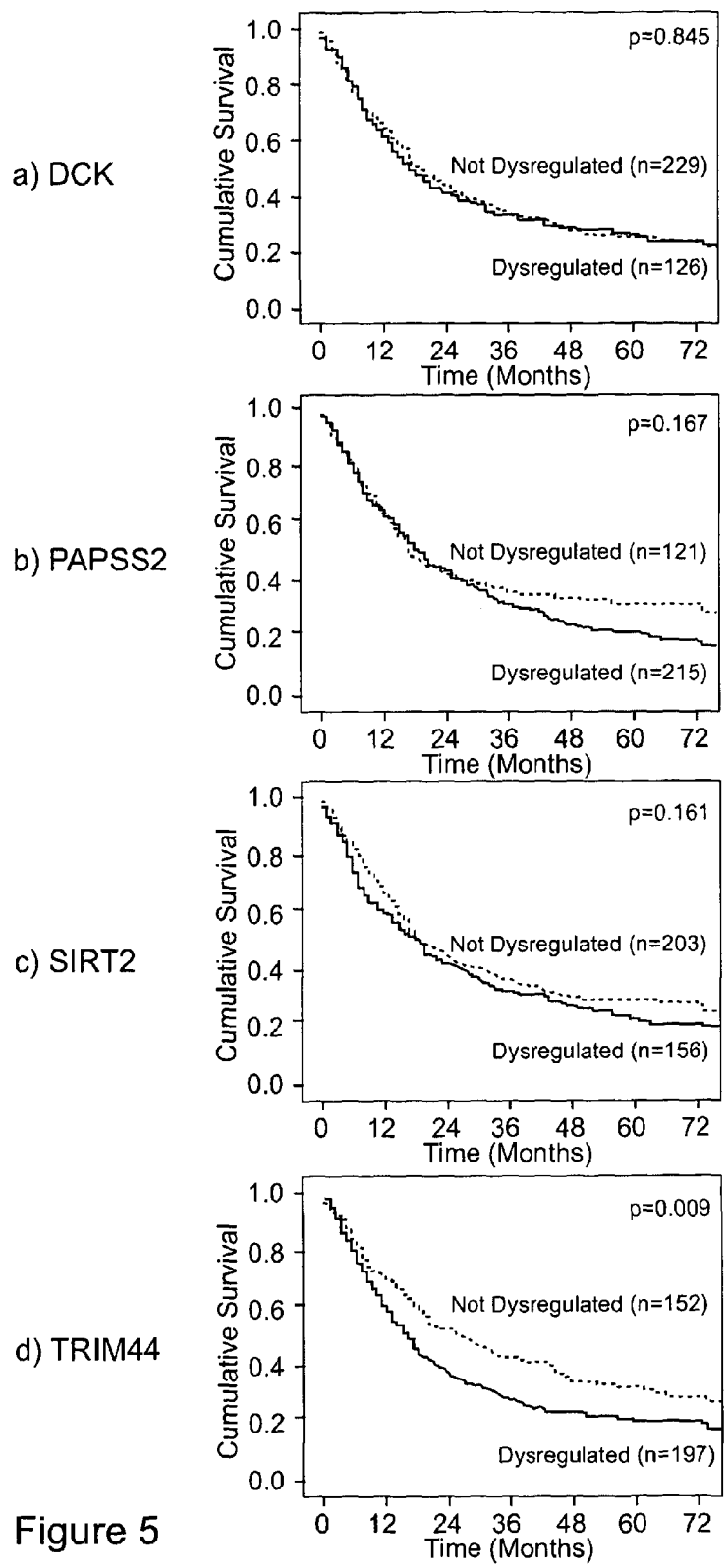
FIG. 5—Kaplan-Meier plots of survival comparing external validation patients with dysregulation and no dysregulation of a) DCK ($\chi^2$LR=0.038, 1 d.f., P=0.85), b) PAPSS2 ($\chi^2$LR=1.91, 1 d.f., P=0.17), c) SIRT2 ($\chi^2$R=1.97, 1 d.f., P=0.16), and d) TRIM44 ($\chi^2$LR=6.86, 1 d.f., P=0.009). Crosses represents censored data, P-values calculated using the log rank (Mantel-Cox) test.
Figure 6:
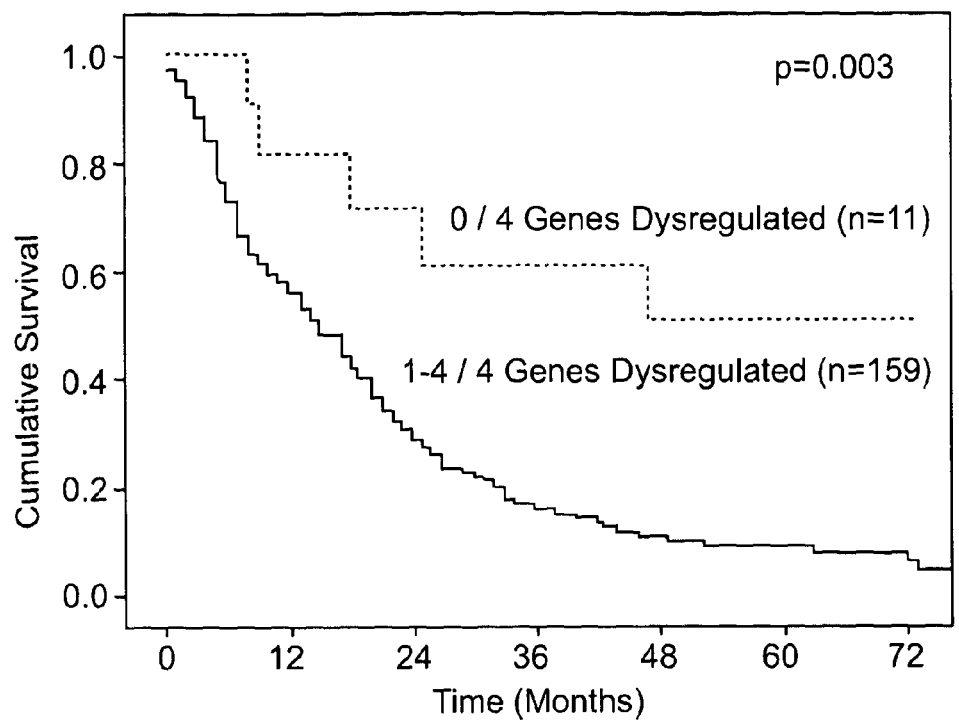
FIG. 6—Kaplan-Meier plots of survival comparing external validation patients staged T3 N1 with none of the four genes dysregulated and those with any of the four genes dysregulated ($\chi^2_{LR}$=9.07, 1 d.f., P=0.003). Crosses represents censored data, P-values calculated using the log rank (Mantel-Cox) test.

At an individual gene level TRIM44 was independently prognostic in the external validation dataset. Patients with dysregulation of TRIM44 (200/355, 53.9%) had a median survival of 16 months (95% CI 13-19 months) compared with 27 months (95% CI 19-35 months) for those without dysregulation ($\chi^2_{LR}$=6.86, 1 d.f., P=0.009, FIG. 5d). There was a non-significant trend for patients with dysregulation of PAPSS2 and SIRT2 to do worse than those with no dysregulation (FIG. 5b-c) but there was no evidence that DCK was individually prognostic (FIG. 5a). Despite this removal of any of the four genes from the signature TRIM44, SIRT2, PAPSS2 and DCK reduced its prognostic power.

When TNM stage, differentiation, resection margin status, neurovascular invasion and the four gene TRIM44, SIRT2, PAPPS2 and DCK molecular prognostic signature were entered into a multivariable Cox regression model, the four gene signature remained in the final model along with T and N-stage (P=0.013) demonstrating its independent prognostic power (table 5).

Example 3

Comparative Genomic Hybridisation And Matched Gene Expression Profiling Study

Integrative analysis of array comparative genomic hybridisation and matched gene expression profiling data reveals novel genes with prognostic significance in oesophageal adenocarcinoma The incidence of oesophageal adenocarcinoma (OAC) has been increasing rapidly with a dismal survival rate of less than 20%. Understanding the genomic aberrations and biology of this cancer may enhance disease interventions. This study aimed to use genome-wide genomic and expression data to enhance the understanding of OAC pathogenesis and identify groups with differential outcomes.

Methods: Array-comparative genomic hybridisation (aCGH) analysis was carried out on 56 fresh frozen OAC resection samples with long-term clinical follow-up data. Samples with aberrations were further analysed with whole-genome single-nucleotide polymorphism arrays to confirm aCGH findings. Matched gene expression microarray data were used to identify genes with high copy number-expression correlations. Nested-multiplex PCR on DNA from microdissected specimens and fluorescence in situ hybridisation (FISH) assays were used for targets validation. Immunohistochemistry (IHC) on the same cohort and independent samples (n=371) was used for subsequent validation. Kaplan-Meier survival analyses were performed based on aCGH data after unsupervised K-means clustering (K=5, 50 iterations) and IHC data. Results: aCGH identified 17 common regions (>5% samples) of gains and 11 common regions of losses, including novel regions in OAC (loci 11p13 and 21q21.2). Integration of aCGH data with matched gene expression microarray data highlighted genes with high copy number-expression correlations: two deletions (p16/CDKN2A, MBNL1) and four gains (EGFR, WT1, NEIL2, MTMR9). IHC demonstrated protein over-expression of targets with gains: EGFR (10%), WT1 (20%), NEIL2 (14%) and MTMR9 (25%). These targets individually (p<0.060) and in combination had prognostic significance (p=0.008). On the genomic level, K-means clustering identified a cluster (32% of cohort) with differential $\log_2$ ratios of 16 CGH probes ($p<4\times10^{-7}$) and a worse prognosis (median survival=1.37 years; p=0.015).

Conclusions: Integration of aCGH and gene expression data identified copy number aberrations and novel genes with prognostic potential in OAC.

Using unsupervised clustering of array-comparative genomic hybridisation (CGH) data, we discovered 16 CGH probes including 6 novel genes that conferred a poorer prognosis to a subgroup of oesophageal adenocarcinoma patients.

We integrated genome-wide datasets from array-comparative genomic hybridisation and gene expression microarray profiling in this study, and identified three novel molecular targets not previously associated with oesophageal adenocarcinoma: WT1, NEIL2 and MTMR9. This is the largest cohort of individuals with OAC to be investigated using aCGH to date, which has combined genome-wide aCGH and gene expression microarray data.

Extensive validation showing amplifications and subsequent over-expression of our targets (EGFR, WT1, NEIL2, MTMR9) in 10-25% of our patient cohort and an independent cohort demonstrated the ability of these targets to stratify patients into different prognosis groups.

Novel molecular targets identified from our study may be used as prognostic biomarkers to enhance clinical management of patients with oesophageal adenocarcinoma, by stratifying patients into different survival groups. In addition, like EGFR in lung cancer, some of these targets such as WT1 and NEIL2 have the potential to be exploited therapeutically in the future.

Oesophageal adenocarcinoma (OAC), including tumours of the gastroesophageal junction, has increased 6-fold in the West over the last 30 years.[1] Its rapid rise in incidence is compounded by its poor prognosis, with a five-year survival of <10%.[2] This poor outcome reflects the late presentation and current limitations in clinical management of these patients. An understanding of the molecular changes underlying this cancer is anticipated to lead to improved clinical management and outcomes.

Chromosomal aberration is one of several mechanisms that can lead to gene dysregulation and has long been known to play a critical role in the pathogenesis of human cancers.[3] The identification of regions of genomic gains and losses has resulted in the discovery of novel oncogenes[4] and tumour suppressor genes (TSGs) respectively.[5] Similar to other cancers, common high level-amplifications (25% of cases) have been frequently reported in OAC. The common regions of amplification on 8q (37% of cases)[6] and 17q (39% of cases)[7] map to the oncogenes v-myc myelocytomatosis viral oncogene homolog (C-MYC) and v-erb-b2 erythroblastic leukemia viral oncogene homolog 2 (ERBB2). Whilst the exact role of MYC in the pathogenesis of OAC is not defined, ERBB2 amplifications have been shown as a promising target for personalised treatment in the ToGA trial.[8] One of the best characterised chromosomal aberrations in OAC is the loss of heterozygosity (LOH) of the TSG TP53 (>50% of cases), which is a powerful predictor of disease progression.[9] Finally, two genes frequently reported to have homozygous deletions (HDs) in OAC are the well-known TSG p16/CDKN2A (20% of cases, with co-deletion of MTAP)[10-11] and fragile histidine triad (FHIT) (20-50% of cases).[12-14] In addition to being early indicators of OAC development, targeting HDs may lead to improved treatment regimes for OAC patients with these deletions, as tested in clinical trials for MTAP-deficient tumours.

In the past decade, DNA copy number gains/amplifications on chromosomes 1q, 3q, 7p, 7q, 8q, 17q and 20q along with copy number losses (including LOH and HDs) on 3p, 4q, 5q, 9p, 14q, 16q, 17p and 18q have been reported in OAC using genome-wide approaches (summarised in table S.1). Array-comparative genomic hybridisation (aCGH) has proven to be an extremely useful tool in identifying novel molecular targets. Following our hypothesis that alterations in copy number that affect gene expression levels will likely to modify protein expression, the integration of expression data with copy number changes allows the changes most likely to be causally implicated in tumour evolution to be identified. Therefore, for the first time in OAC, data from an aCGH platform were integrated with corresponding gene expression microarray profiles of 56 fresh frozen OAC resection samples in this study. Following integrated analysis of aGH and expression data, only targets with significant expression changes following copy number aberrations were further validated on the DNA and protein level, and tested for prognostic relevance. Finally, samples were segregated into groups with similar copy number profiles and a cluster with a significantly worse prognosis was identified.

Materials and Methods

Sample Collection

During June 1992-June 2000, 56 snap frozen samples from oesophago-gastric cancer patients undergoing resection with curative intent were collected by Prof. Derek Alderson (Bristol Royal Infirmary). Clinical information of these patients were summarised in table S.2. All clinical diagnoses were confirmed by two expert pathologists according to recommended guidelines.

Patients

The clinical data for the 56 OAC patients are shown in table S.2. The average age at diagnosis was 69 years (range: 45-89) and the minimum follow-up was 5 years for surviving patients. There was a range of disease stages and differentiation grades (few patients with stage 1V disease since oesophagectomy was performed with curative intent). In keeping with the historical nature of the cohort, the majority (53/56) of the patients did not have prior chemotherapy treatment giving an unbiased assessment of genomic aberrations.

aCGH Analysis

All samples prepared for aCGH had >70% tumour cellularity. DNA was extracted from ten 30 μm sections of each tumour using standard protocols (supplement S.3). Labelling was performed using BioPrime DNA labelling kit reagents (Invitrogen, Carlsbad, Calif.) according to protocols described previously.[16] Labelled OAC DNA samples were hybridised, along with a common reference sample obtained from a pool of 20 leukocyte DNA samples of the same sex, to customised 60-mer oligonucleotide microarrays containing 28830 unique map positions (Human May 2004 assembly (hg17)).[17] Combined colour switch experiments were performed, whereby labels for DNA from human male and female were reversed, to generate precise ratios for these experiments: mean $log_2$ ratio=0.03 and standard deviation (SD)=0.29. Data from aCGH experiments were processed using BlueFuse (v3.4 Build m 5836; BlueGnome, Cambridge, UK) and analysed using the snapCGH Bioconductor package within the R statistical framework (version 2.3.1). Normalised data for the 56 tumours described in this study are available from Gene Expression Omnibus (GEO) database (GSE20154). Data from aCGH were normalised after background-substraction using region detection algorithm swatCGH available at an internet site hosted by the University of Cambridge School of Biological Sciences), which was then used to detect common regions (5% samples) of aberrations covering ≥5 oligonucleotides. This threshold was used to allow a comprehensive analysis of genomic aberrations present whilst eliminating those only affecting one or two cases.

Gene Expression Microarray Profiling

Gene expression microarray analysis of the RNA from these tumours was performed previously (GEO accession number GSE19417).[18] In brief, RNA was extracted from ten 30 μm sections of each tumour using Trizol™ according to manufacturer's instructions (Invitrogen, Carlsbad, Calif.). Extracted RNA was then amplified using a modified MMLV-RT-mediated reverse-transcription protocol or a 2× UniAmp protocol using a modification of Ambion's MessageAmp II kit (Ambion, Applied Biosystems). Resulting RNA was labelled with cyanine dyes and hybridised to a custom made Agilent 44K 60-mer oligo-microarray (Agilent Technologies, Santa Clara, Calif.). Data from expression arrays were then normalised using external spike-in controls.[18]

SNP Array

In view of advances in available technology, Illumina Human CytoSNP-12 Bead array v2.0 was used for validation purposes of nine selected cases post-aCGH analysis (following manufacturer's protocol). Briefly, 500 ng of genomic DNA extracted from frozen tumour tissues were denatured and amplified at 37° C. overnight. The amplified DNA was fragmented and precipitated at 4° C., resuspended in hybridisation buffer, and hybridized to Human CytoSNP-12 chips at 48° C. overnight. Non-hybridised DNA and nonspecific hybridisation were washed away, and captured DNA was used as template for one-base extension of the locus-specific oligos on Bead Chips. All SNP data were analysed and exported by Bead Studio v2.0 (Illumina). SNP data of this study are publicly available (GEO accession number GSE 25201).

Integrated Analysis of aCGH and Gene Expression Profiling Data

All genes within identified common regions of aberrations from aCGH data were matched to their respective expression levels based on expression microarray profiles. Genes whose expression levels were >1.5-fold up/downregulated in tumours with aberrations were plotted against their respective aCGH log2 ratios to select genes with best copy number-expression correlations. Genes displaying a high correlation between expression and DNA copy number (log2 ratio>0.32, i.e. mean log2 ratio+SD; and fold-change >6.5, i.e. greater than 4×1.5-fold change) were further classified to justify their importance in OACusing Santarius et. al's approach,[19] which classifies the relevance of genomic and expression changes in genes. Identified targets were validated using IHC assays.

Lasermicrobeam Microdissection (LMM) and Nested-Multiplex PCR

LMM on 7 μm cryostat sections of frozen OAC sample stained with cresyl violet (Fisher Scientific, Pittsburgh, Pa.) was carried out using the Zeiss P.A.L.M. Laser MicroBeam system (Microlaser Technologies GmbH, Bernried, Germany) following the procedure described previously.[20] Selected areas with tumour cells were specifically removed from the sections and transferred to a 0.5 ml microfuge tube cap for subsequent DNA extractions. Microdissected cells were incubated in Proteinase K buffer (10 mM Tris pH 7.4, 10 mM EDTA, 150 mM NACl and 0.4% SDS) and 40 μg/ml Proteinase K (Invitrogen, Carlsbad, Calif.) at 65 C (1 hour) and then at 37 C (overnight). DNA extraction was carried out using standard phenol/chloroform extraction method. Multiplex PCR was carried out with standard PCR conditions, using 1 mM of primers of the genes of interest, alongside a control primer pair (AQP3). Nested-multiplex PCR uses two rounds of PCR for greater genomic DNA amplification. Second round PCR was carried out using products from first round PCR diluted 1:20 using nuclease-free water. Detailed protocols are available in supplement S.3. Products from nested-multiplex PCR were sequenced to confirm results (figure S.4).

FISH on Tumour Touch-Imprints

Touch-imprints were produced by touching frozen tumour samples onto the surface of poly-L-lysine coated slides (Polysciences, Inc. Baden-Württemberg, Germany), air-drying (10 minutes), fixing in 3:1 methanol:acetic acid (15 minutes), dehydrating in ethanol series (70%, 90%, 100%; 3 minutes each) and incubating in dark at 37° C. (overnight). BACs (CHORI BACPAC Resources, Oakland, Calif.) and DNA from plasmids probing for centromeres (Resources for Molecular Cytogenetics, University of Bari, Italy) were labelled indirectly by nick-translation method using digoxigenin-/biotin-labelled dUTPs (Roche, Lewes, UK). Detection was carried out using sheep FITC-conjugated anti-digoxigenin (Roche, Lewes, UK)/Cy5-conjugated streptavidin (GE Healthcare, Amersham, UK) and goat-biotinylated anti-streptavidin (Vector Labs, Peterborough, UK) antibodies. 100 nuclei per slide were counted for analysis of HD. Metaphase preparation of lymphocyte cell line DRM/M62 was used as positive controls for all FISH assays (data not shown), whereby two paired centromere-target gene FISH signals were detected in all nuclei and metaphase chromosomes. See supplement S.5 for probe and imaging details.

Immunohistochemistry on Tissue Microarrays (TMAs)

TMAs available represent 2 mm×2 mm areas in triplicates typical for the tumour as identified by expert gastro-intestinal pathologists. TMAs of samples from external datasets (n=371) were available resulting from collaboration with the Oesophageal Cancer Clinical and Molecular Stratification (OCCAMS) study group.[18] IHC was performed on a Bond™ System (Leica Microsystems (UK) Ltd, Milton Keynes, UK) according to manufacturer's recommendations after confirming antibody specificities by Western blotting (data not shown), followed by optimisation on positive control cell blocks and oesophageal tissue sections. For antibody sources and detailed scoring of IHC assays see supplement S.6.

External Validation of aCGH Signature

Copy number information was obtained from Nancarrow et. al's[14] dataset (GEO accession number GSE 10506). This is the only aCGH dataset currently publicly available with patient survival information. Following Nancarrow et. al's thresholds for genomic gains (log R>0.2) and losses (log R<−0.35), each CGH clone was scored (table S.7) and subsequently analysed to determine their prognostic significance.

Statistics

Unsupervised hierarchical clustering (50 iterations) using K-means clustering method was performed using average linkage, euclidean distance measure, K=5 (reproducibility >50%; Gene Cluster 3.0, C Clustering Library version 1.47). Fishers exact test was used to compare clinical variables of the clusters generated and a modified t-test (with adjusted Bonferroni correction) was employed to identify CGH probes with significantly different $\log_2$ ratios. Survival differences were assessed using log-rank test. Statistical significance was set at p<0.050.

Results

ACGH Identifies Novel Genomic Regions of Aberrations

Figure 8:
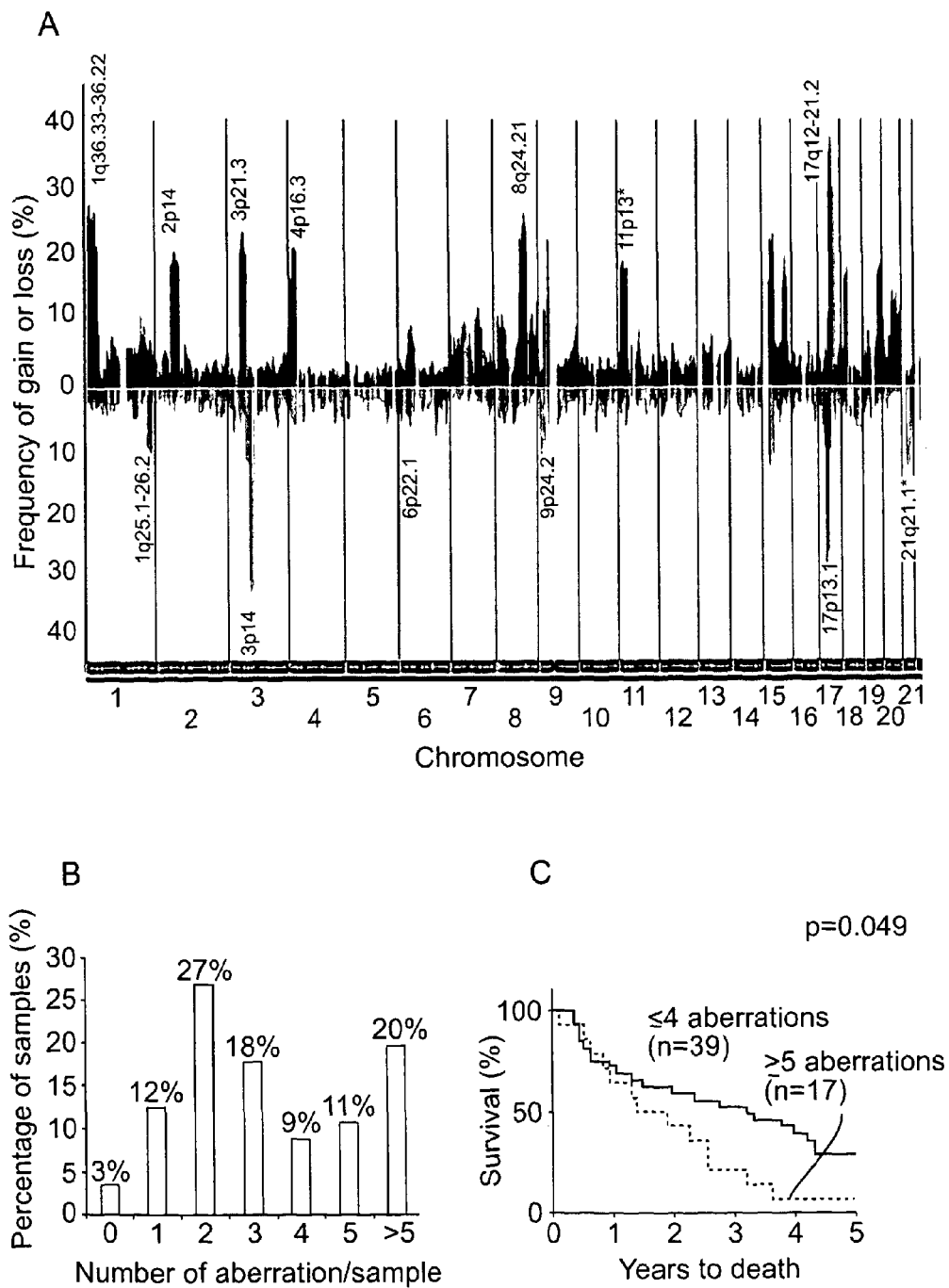
FIG. 8 A) Frequency of all significant gains and losses (>5% of samples). Bars above x-axis denote copy number gains and bars below x-axis indicate copy number losses. Chromosomal boundaries are denoted by vertical lines and chromosomes are represented along the x-axis. The loci most frequently gained (>20% of samples) and lost (>10% of samples), as well as novel loci (asterisked), are annotated. Sex chromosomes were excluded in our analysis and hence not shown. B) Correlation between recurrent aberrations and survival: Breakdown of samples having different numbers of aberrations based on 28 common regions identified, and C) Kaplan-Meier plot of OAC patients grouped according to the number of common regions of aberrations involved per sample.

Genomic gains and losses were detected on all chromosomes. The mean frequency of gains across the whole genome was 11% (standard error of mean, SEM=0.4%, 95% CI: 9.9-12.1%) and the mean frequency of losses was 8.2% (SEM=0.5%, 95% CI: 7.1-9.3%; FIG. 8A). Analysing these data revealed 28 common regions of aberrations (regions and genes with >1.5-fold expression changes are listed in tables 1A and 1B). Based on the 28 common regions of aberrations identified. 69% of samples had <5 copy number alterations (FIG. 8B). The group with ≤5 alterations (31% of samples) had a significantly poorer clinical prognosis (p=0.049; FIG. 8C).

Figure 9:
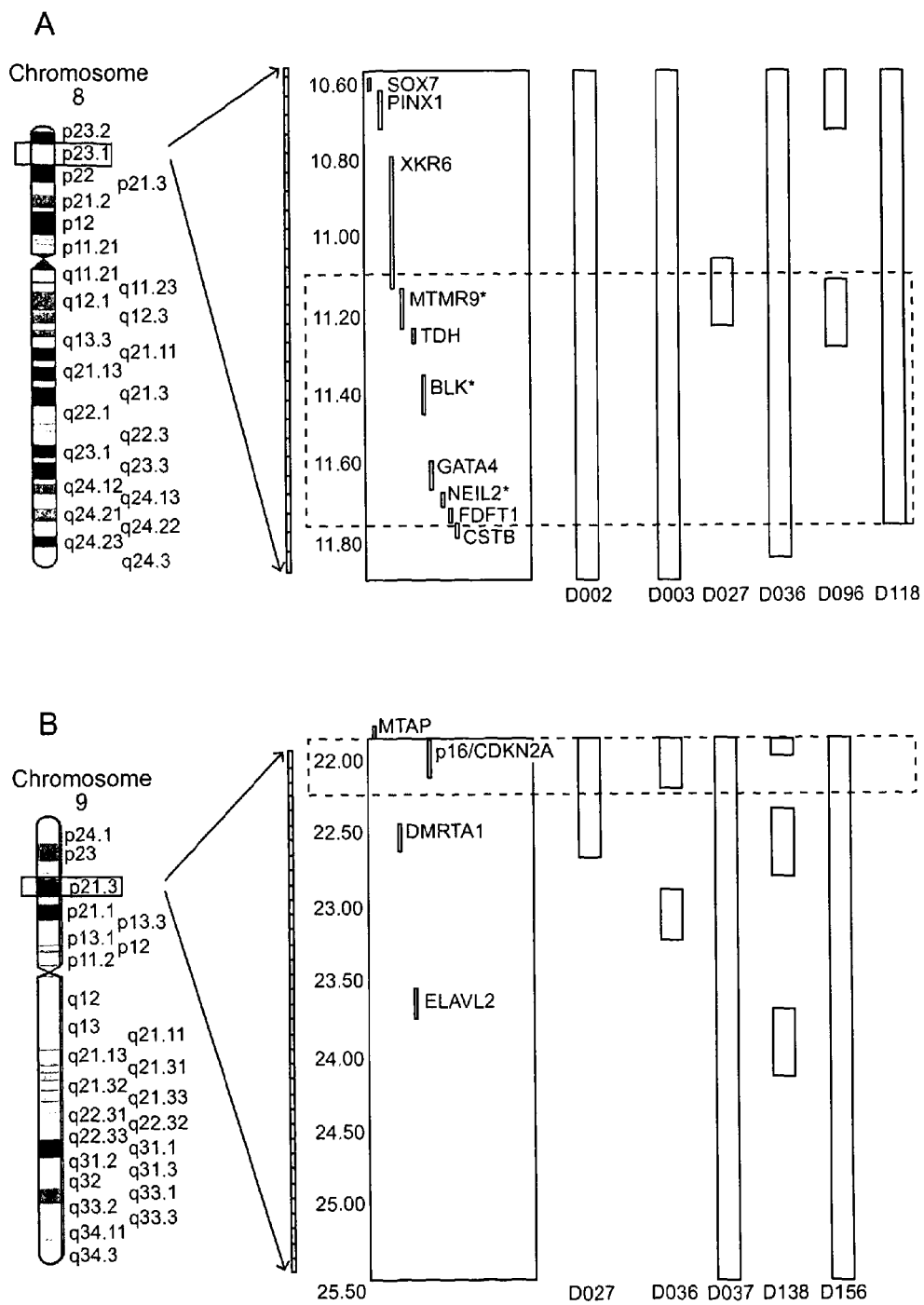
FIG. 9 Detailed region mapping analysis using data from SNP array (Human May 2004 assembly (hg17)): A) Six samples known from aCGH to have genomic gains at locus 8p23.1 (10.58-11.78 Mb) encompassing two validated genes based on integrated analysis of aCGH and gene expression profiling data: MTMR9 and NEIL2. Bars denote 2-4 copies of genes; and B) Five samples known from aCGH to have genomic losses at locus 9p21.3 (22.00-22.50 Mb). Bars denote 0-1 copies of genes. Dashed box highlights the region involving the most overlap between samples.

The chromosomal regions most. frequently gained were loci 1p36.33-36.22 (34%), 3p21.31 (25%), 8q24.21 (28.6%) and 17q12-21.2 (46%), whilst those frequently lost were 3p14 (39%) and 17p13.1 (34%). These loci contain genes previously known to be associated with OAC: C-MYC, ERBB2, FHIT and TP53. aCGH findings, including the frequency of aberrations, were subsequently confirmed by a high-density SNP array analysis on 9 tumour samples, previously identified from aCGH analysis to harbour gains on locus 8p23.1 and losses on locus 9p21.3 (FIG. 9). In addition to the regions previously reported in genome-wide studies of OAC (table S.1), novel loci for OAC at 11p13 which contained genomic gains (11% of samples) and at 21q21.2 (11% of samples) which contained genomic losses were identified. Within locus 11p13, genes such as Wilms tumour 1 (WT1), catalase (CAT) and CD44 have previously been implicated in breast and lung cancers.[21-23] Locus 21q21.1 contains genes that have been implicated in tumourigenesis such as the ubiquitin specific peptidase 25 (USP25), downregulated in lung cancers[24] and coxsackie virus and adenovirus receptor (CXADR), a putative TSG lost during gastric cancer progression.[25]

| Cytoband | (Mb) | Frequency (%) | # genes | Genes differentially expressed |
|---|---|---|---|---|
| Table 1A Common regions (≥5% samples) of genomic gains. | | | | |
| 1p36.23-36.22 | 7.9-11.0 | 19/56 (33.9) | 31 | RPL22, TNFRFSF25, ERRFI1, PIK3CD, RBP7, APITD1 |
| 1p22.1-21.3 | 92.0-94.8 | 8/56 (14.3) | 28 | RPL5, F3 |
| 1q25.1 | 170.2-174.3 | 6/56 (10.7) | 14 | DARS2, SERPINC1 |
| 2p14 | 64.0-70.5 | 12/56 (21.4) | 27 | MEIS1 |
| 3p21.31 | 44.7-46.9 | 14/56 (25.0) | 28 | — |
| 4p16.3 | 0.6-1.2 | 13/56 (23.2) | 12 | DGKO |
| 6p21.1-12.3 | 43.0-47.6 | 15/56 (26.8) | 50 | GTPBP2, MRPL14, RUNX2, CLIC5, CYP39A1, CD2AP |
| 6p22.1 | 27.2-27.5 | 6/56 (10.7) | 6 | — |
| 7p11.2 | 54.6-57.4 | 6/56 (10.7) | 18 | SEC61G, EGFR, GBAS, PSPH, CCT6A |
| 7q21.3-22.1 | 97.4-99.4 | 7/56 (12.5) | 28 | BAIAP2L1, CYP3A5 |
| 8p23.1 | 9.8-11.7 | 6/56 (10.7) | 16 | PPP1R3B, MSRA, SOX7, XKR6, MTMR9, NEIL2, FDFT1 |
| 8q24.21 | 36.6-38.0 | 16/56 (28.6) | 4 | C-MYC |
| 11p13 | 32.0-35.2 | 6/56 (10.7) | 26 | WT1, CD59 |
| 15q24.1 | 71.8-73.0 | 6/56 (10.7) | 5 | — |
| 17q12-21.2 | 33.8-37.3 | 26/56 (46.4) | 73 | RPL23, ERBB2, GRB7, CSF3, CASC3, CDC6, RARA, IGFBP4, SMARCE1 |
| 19q13.42-13.43 | 60.5-63.8 | 6/56 (10.7) | 83 | — |
| 20q13.12 | 43.0-43.5 | 5/56 (8.9) | 18 | TOMM34, MATN4, SDC4 |
| Table 1B Common regions (≥5% samples) of genomic losses. | | | | |
| 1q21.1 | 142.4-148.0 | 3/56 (5.4) | 86 | PDE4DIP, NOTCH2N, PEX11B, POLR3C, TXNIP, PDZK1, FMO5 |
| 1q25.1-25.2 | 172.5-174.6 | 6/56 (10.7) | 6 | — |
| 2q36.1-36.2 | 221.9-225.0 | 3/56 (5.4) | 13 | EPHA4, SCG2, SERPINE2 |
| 3p14 | 58.2-62.7 | 22/56 (39.3) | 16 | FHIT |
| 3p21.31 | 49.7-51.2 | 8/56 (14.3) | 35 | EIF2A |
| 3q23-25.1 | 150.4-153.5 | 4/56 (7.1) | 29 | MBNL1 |

-continued

| Cytoband | (Mb) | Frequency (%) | # genes | Genes differentially expressed |
|---|---|---|---|---|
| 6p22.1 | 26.2-26.4 | 8/56 (14.3) | 24 | — |
| 9p24.2 | 2.7-4.6 | 6/56 (10.7) | 8 | — |
| 9p21.3 | 22.0-25.5 | 5/56 (8.9) | 4 | p16/CDKN2A |
| 17p13.1 | 7.43-7.62 | 19/56 (33.9) | 11 | — |
| 21q21.1 * | 16.1-22.4 | 6/56 (10.7) | 10 | — |

* indicates a novel region not previously reported in OAC. In bold: Regions with potential gains/amplifications ($\log_2$ ratios > 0.61), or homozygous deletions ($\log_2$ ratios < −0.55).

Integrative Analysis of Copy Number and Gene Expression Data

Figure 10:
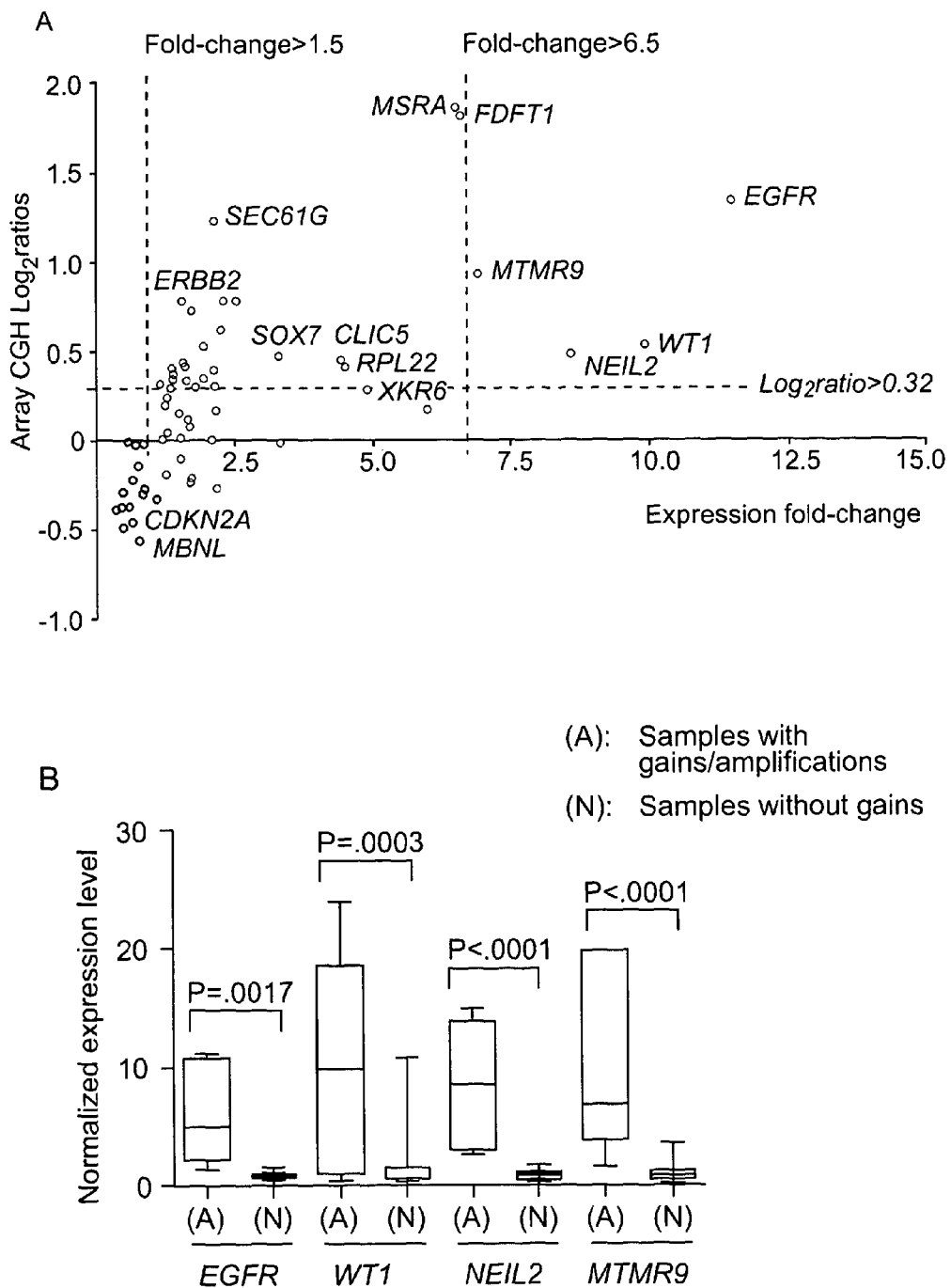
FIG. 10 A) Scatter plot shows correlation between DNA copy number changes and gene expression levels of individual genes within regions with genomic gains/losses (listed in tables 1A/B). Open circles represent genes within common regions of gains and filled circles represent genes within common regions of losses. 4 genes that fulfilled the most stringent criteria ($\log_2$ ratios >0.32 and expression fold-change >6.5): EGFR, WT1, NEIL2 and MTMR9, were brought forward for validation. B) Box plots show patterns of gene expression levels of each selected gene (EGFR, WT1, NEIL2 and MTMR) in all OAC samples, showing statistically significant differences between samples having genomic gains/amplifications and those without (t-test p<0.005).

To explore the significance of genomic aberrations identified, criteria proposed by Santarius et al.[19] that categorise the importance of genes according to their copy number and expression levels were followed to identify genes with differential expression levels following genomic aberrations. Data from aCGH ($\log_2$ ratios) were matched to the gene expression microarray profile (median expression fold-change of genes within regions with gains). Using a cut-off of >1.5 fold-change in expression level, 64 genes were shortlisted (FIG. 10A and table S.8). Most of the genes within locus 8p23.1 common region of amplifications (MSRA, FDFT1, SOX7 and XKR6) have elevated expression levels accompanying genomic gains. By applying cut-offs of $\log_2$ ratio >0.32 (threshold for gain) and expression fold-change >6.5 (a more stringent threshold for over-expression), genes with the most significantly increased expression levels following genomic gains were WT1 at the novel locus 11p13 (10-fold), epidermal growth factor receptor (EGFR; 11-fold), and two novel genes within locus 8p23.1: nei-like 2 (NEIL2) and myotubularin related protein 9 (MTMR9) (>6.5-fold) were highlighted (FIG. 10B). According to Santarius et al.,[19] EGFR is a class III gene as it is amplified, over-expressed and has clinical implications. The other three are class IV genes, which are genes within regions of genomic gains that are over-expressed, which may have potential roles in cancer development. The regions identified with potential HDs were loci 3q23-25 and 9p21.3. Locus 3q23-25 (7% of samples) contains a potential HD involving muscleblind-like 1 (MBNL1) whilst locus 9p21.3 (9% of samples) harbours important genes including p16/CDKN2A, MTAP and a novel gene ELAVL2, whose function is unknown.

Validation of Targets from Integrative Analysis

Figure 11:
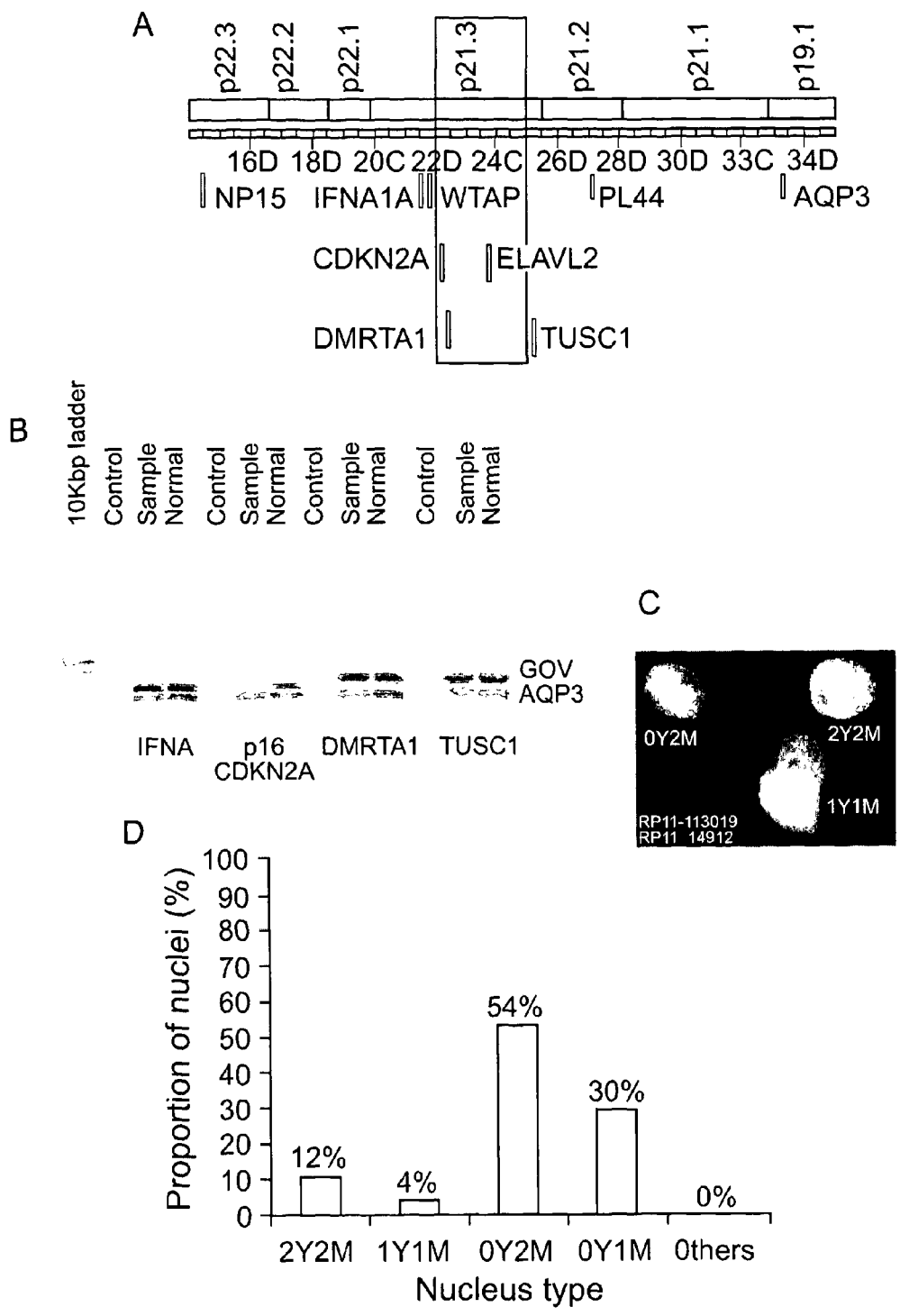
FIG. 11 Validation of 9p21.3 HD on a representative OAC sample: A) Schematic illustration of the 9p21.3 region depicts relative genomic positions of genes within the potential HD region (boxed) and flanking genes. B) A representative gel image illustrating nested-multiplex PCR analysis on microdissected DNA showing deletion of p16/CDKN2A. STS marker for AQP3 was used as a control alongside the markers for genes of interest (GOI: IFNA, p16/CDKN2A, DMRTA1 and TUSC1). C) A representative image (100× magnification) of FISH on tumour touch-imprints to confirm HD of p16/CDKN2A. Categories of nuclei included: 2 paired yellow and magenta signals (2Y2M); 1 yellow and 2 green signals (1Y2M); paired magenta signals (0Y2M); 1 magenta signal (0Y1M); others. D) Graph illustrates quantitative analysis of FISH assays based on 100 nuclei counted per sample. The proportions of nuclei are quoted in percentage in parentheses and the types of nuclei are marked along the x-axis. The lack of yellow signals indicates loss of p16/CDKN2A. Note: Genes of interest (GOI); Aquaporin 3 (AQP3) control gene.

For HDs, locus 9p21.3 was further validated (FIG. 11A). First, microdissection was carried out to remove most stromal cells from the tumour section. Nested-multiplex PCR on p16/CDKN2A and three adjacent genes showed that p16/CDKN2A was the only gene completely deleted (FIG. 11B) and the products were sequenced to confirm identity of p16/CDKN2A (figure S.4). FISH on interphase nuclei demonstrated that >80% of nuclei had lost both copies of the p16/CDKN2A gene, in agreement with the tumour cellularity and heterogeneity of sample (FIG. 11C, D). Although p16/CDKN2A loss is well established in OAC this was a useful validation of the aCGH data.

Figure 12:
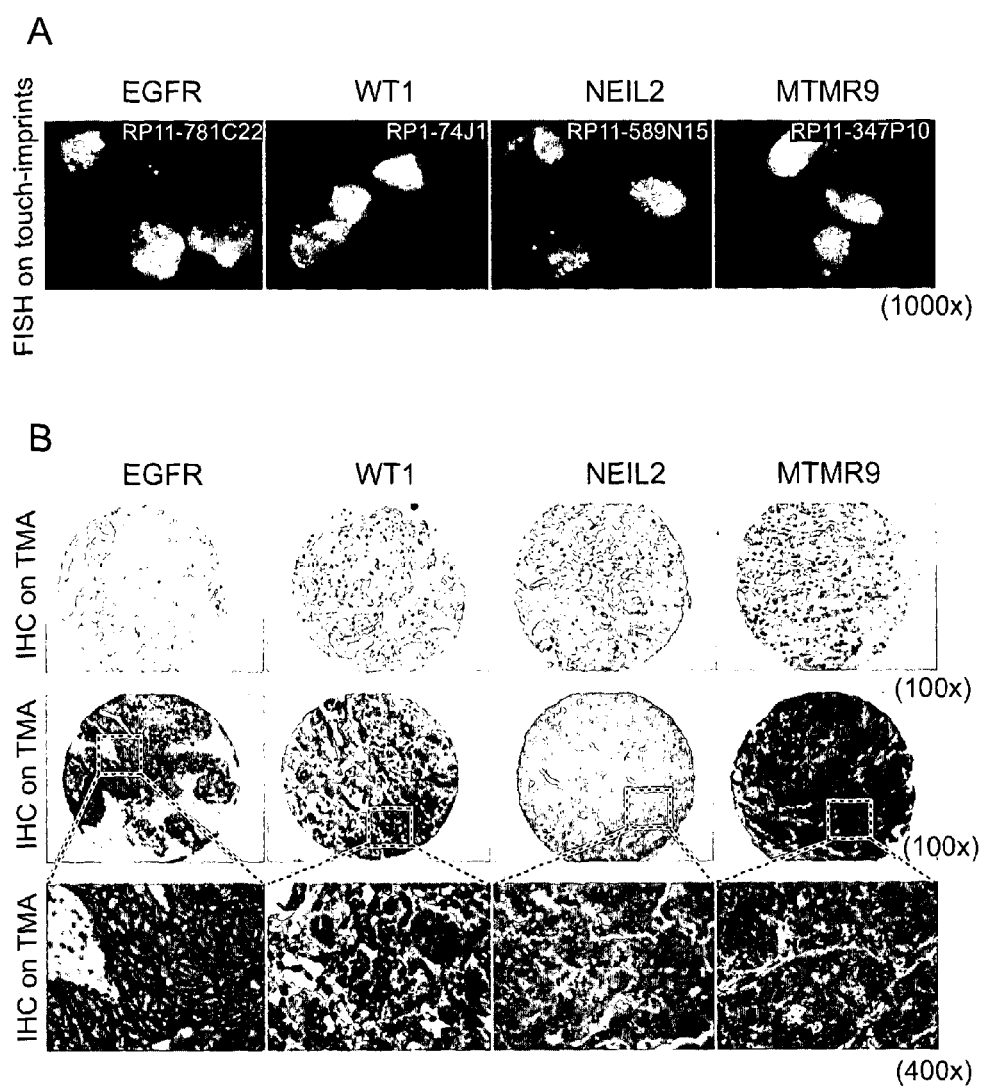
FIG. 12 Validation of genomic gains and protein over-expression involving EGFR, WT1, NEIL2 and MTMR9: A) FISH images on tumour touch-imprints showing interphase nuclei with gene amplifications: BACs containing genes of interest were shown yellow and centromeric controls were magenta (1000× magnification). B) Representative IHC images from tumours without genomic amplifications (top panel, 100× magnification) and from tumours with genomic amplifications and over-expression (middle and bottom panels: magnifications at 100× and 400× respectively).

For regions of gains, genes with the highest gene expression fold-changes expression (EGFR, WH, NEIL2 and MTMR9) were validated. These criteria excluded genes such as ERBB2, SEC61G, CLIC5 and RPL22 with relatively high CGH $\log_2$ ratios but minimal expression changes. FISH on tumour touch-imprints confirmed amplifications (ratios of >6 copies per centromere, indicating high-level amplifications of target genes) of all 4 genes in all samples identified by aCGH analysis to harbour these aberrations (FIG. 12A). Subsequent IHC analyses on the same tumours on TMAs confirmed over-expression of these proteins in the same samples (FIG. 12B). Finally, IHC analysis on a large validation cohort of independent OAC (n=371) demonstrated that MTMR9 was most commonly over-expressed, affecting 25% of cases, whereas over-expression of other genes was observed in 21% (WT1), 14% (NEIL2) and 10% (EGFR) of OACs.

Prognostic Significance of Targets

To elucidate the potential clinical significance of our findings, identified candidate genes and an aCGH signature were correlated with prognosis.

Figure 13:
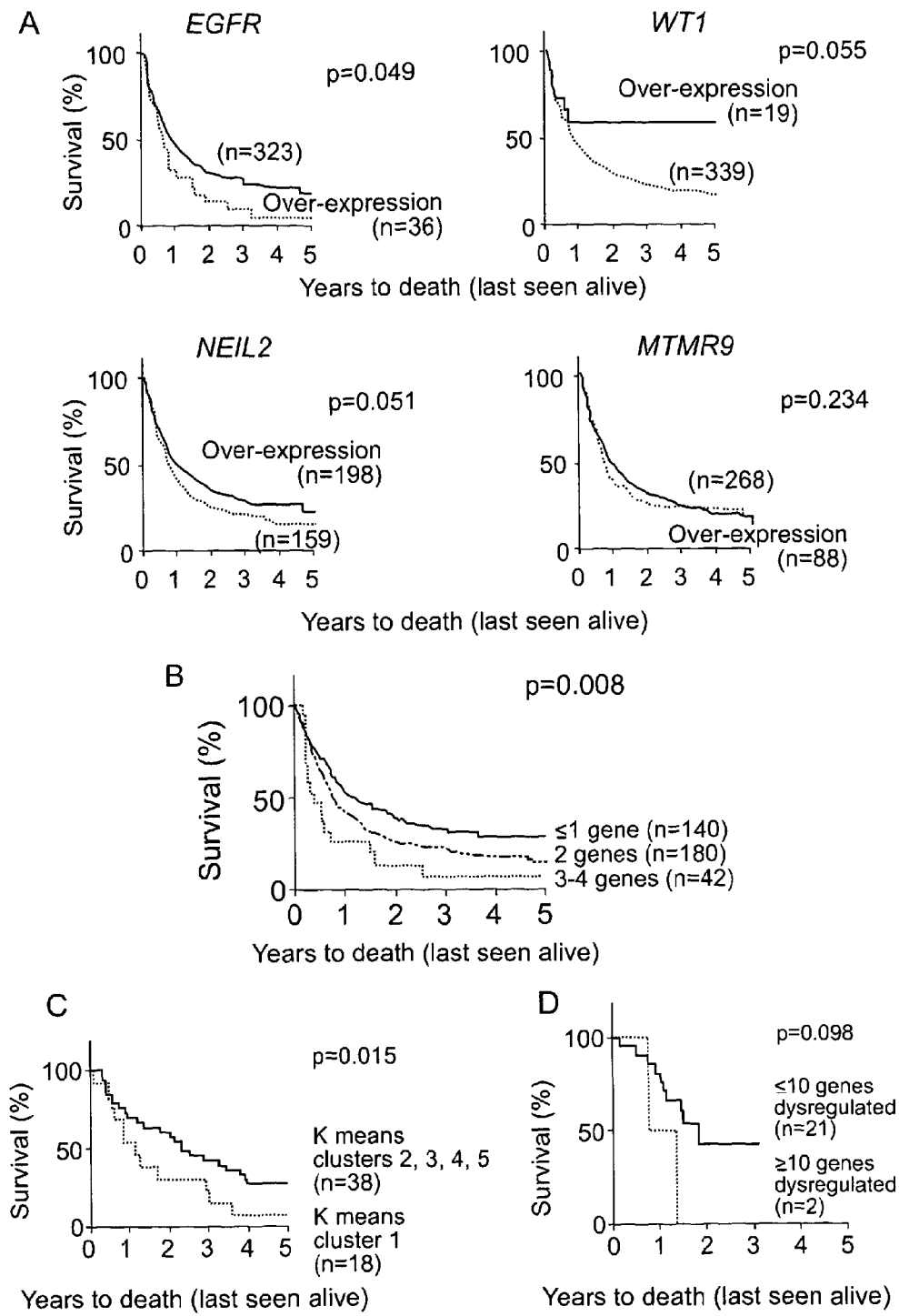
FIG. 13 A) Kaplan-Meier plots of OAC patients on independent datasets (n=371) to show individual prognostic relevance of 4 validated gene targets. B) Kaplan-Meier plot of OAC patients from independent datasets showing stratification of patient survival according to differential expressions of the 4 genes (EGFR, WT1, NEIL2 and MTMR9), based on IHC scores (p=0.008). C) Analysis following K-means unsupervised clustering of aCGH data: Kaplan-Meier plot of 56 OAC patients. Graph shows survival when samples in K-means cluster 1 (n=18) were compared to the remaining samples in clusters 2, 3, 4 and 5 combined. Cluster 1 had a significantly worse prognosis (median survival=1.37 years; p=0.015, HR=1.802, 95% CI=1.141-3.397). D) Independent validation of prognostic significance of 16 aCGH clones: Kaplan-Meier plot of OAC patients obtained from the Nancarrow et. al dataset illustrates the ability of these genes to stratify patients into good and poor survival groups, despite limited by the small sample size (p=0.098).

Using IHC, over-expression of EGFR (P=0.049) confers a poorer survival in OAC whereas over-expression of WT1 and NEIL2 contributes to better prognosis in patients (p<0.060; FIG. 13A). Combined differential expression of all four target proteins (EGFR, WT1, NEIL2 and MTMR9) segregated patients into three groups with very good prognosis, average prognosis and poor prognosis (p=0.008; FIG. 13B).

Unsupervised K-means clustering based on aCGH data generated 5 clusters (50 iterations, reproducibility >50%; supplement S.9). Cluster 1 (n=18, 32.1% of cohort) had a significantly worse prognosis (median survival=1.37 years; hazard ratio=1.802 (95% CI: 1.141-3.397); p=0.015) when compared to the remaining clusters combined (median survival=2.74 years; FIG. 13C). Fishers exact test showed an increased male:female ratio in cluster 1 (p=0.010) and t-test with adjusted Bonferroni correction identified 16 genes with significantly different log 2 ratios (p<4×10−7) that differentiated cluster 1 from the remaining clusters (table S.10). Among these, three genes reside within the common regions of gains identified earlier (SCAMP2 on 15q24.1, PCBP1 on 2p14 and TSC22D4 on 7q22.1), six novel genes (CEP192, ZMYND15, SYCP2L, PMP2, LYPD6 and MEXD3) and one hypothetical protein (BC040153). A multivariate Cox-regression model for survival including these 16 genes and other clinical parameters (age, sex, T-stage, N-stage, M-stage and tumour differentiation status) ruled out all other parameters except cluster 1 (p=0.034) and N-stage (p=0.011) as being prognostic. The prognostic significance of these 16 genes were validated on an independent dataset 14 (n=23), which was the only public dataset available at present with copy number and survival information (see table S.7 for gene-specific information). Survival analyses illustrated that the group of OAC patients with >10 of these genes dysregulated had a worse prognosis, however the small sample size limited the statistical power of this analysis (p=0.098; FIG. 13D). Unfortunately there are no other independent OAC datasets available for validation. These genes represent a potential prognostic signature for OAC based on genomic aberrations that require further investigation in a larger cohort.

Discussion

The aCGH data presented here confirmed known genomic aberrations in OAC and identified novel common regions of gains and losses. Using an integrated approach to identify genes with differential expressions as a result of genomic aberrations, we confirmed over-expression of a Santarius class III gene EGFR, and three novel Santarius class IV genes, WT1, NEIL2 and MTMR9 at the protein level, suggesting their importance in OAC. We further demonstrated the prognostic importance of these candidate genes and identified 16 aCGH gene probes that contributed to poorer prognosis in 32% of patients.

These findings from aCGH analysis identified most of the main regions of aberrations reported previously (see table S.1). Two novel common regions with copy number changes not previously reported in any genome-wide studies in OAC, loci 11p13 and 21q21.1, were identified. Like gains on locus 17q (46% of samples) involving ERBB2, gains on locus 1p36 are noteworthy due to the large proportion of samples involved (34%). Many genes within the region have been implicated in other cancers, such as SKI,[26] PRKCZ, [27] MIG-6,[28] CTNNBIP1[29] and PARK7.[30] More interestingly, in concordance with previously published data,[31]

Integrative analysis of copy number-expression data from aCGH and gene expression microarray profiling analyses led to identification of key genes in OAC with genomic amplifications followed by elevated gene expression levels and subsequent protein over-expression. This approach can lead to discovery of novel critical genes, but it should be noted that certain genomic events do not directly translate into gene expression changes. For example, as was observed in our study, the lack of correlation between amplifications and elevated RNA levels of ERBB2 has been previously reported despite strong correlation between amplifications and protein over-expression. accumulated frequencies of genomic changes in OAC conferred a survival difference in our cohort, suggesting the importance of individual genomic events and that frequent genomic aberrations with the probability of rearrangements could directly influence patient prognosis.[32]

The four genes (EGFR, WT1, NEIL2 and MTMR9) identified by integrating data from aCGH and gene expression microarray profiles were shown to be over-expressed in 10-25% of OAC. EGFR has established roles in the development of many cancers and is a potential predictor of outcome in OAC. Therefore, when integrating such datasets it should be remembered that RNA and subsequent protein expressions are often also subjected complex post-transcriptional regulations including effects of microRNA and non-coding RNAs.

[33] The proportion of OAC samples with EGFR over-expression in our data was in agreement with the proportion of OACs having EGFR amplifications (11%) in our cohort. Cytoplasmic staining for WT1 has been observed and described previously despite its role as a transcription factor. [34] In contrast to the possible oncogenic role of WT1 suggested by its over-expression,[35] high WT1 expression is associated with a good prognosis in our cohort, indicating that WT1 could be acting as a TSG as shown in prostate cancer.

[36] In addition, many downstream targets of WT1 have been identified which may influence tumour biology.[37-38] Our finding also confirmed data from previous study that reported locus 11p13-15 rearrangements,[39] hinting at a potential mechanism for WT1 amplifications in OAC. Therefore, our data may highlight a particular subgroup of OAC tumours with unexplored downstream effects in OAC. NEIL2 is a newly discovered enzyme involved in DNA damage repair[40] with no known direct link to any cancer. Our finding suggests that the lack of NEIL2 expression in tumours with worse prognosis could be due to an accumulation of cellular DNA damage. MTMR9 belongs to a family of myotubularin related proteins, which are mainly dual-specificity phosphatases. Though not having a phosphatase domain, MTMR9 has been shown to enhance the functions of other MTMR proteins, like MTMR6 and MTMR7.[41-42]

Novel genes were also discovered as genes differentiating cluster 1 based on unsupervised K-means clustering of aCGH data were identified. Some do not appear to have obvious roles in carcinogenesis, but a number could be directly linked to carcinogenesis, like the mitogen-activated protein kinase 8 interacting protein (MAPK8IP2) Identification of these novel genes via our integrated approach in the analysis of genome-wide data and the prognostic significance of these targets suggest that further investigation of the mechanistic roles of these genes in OAC is likely to provide useful insights into the understanding of OAC pathogenesis.

[43] and ceroid-lipofuscinosis, neuronal 8 (CLNB).[44]

The strength of this study was the availability of copy number and expression data from the same patients with the ability to correlate these findings with clinical outcome. This is the largest cohort of individuals with OAC to be investigated using aCGH which has combined both aCGH and gene expression microarray data. The integration of these data identified novel genes which otherwise would not have been selected from analysis of either aCGH or gene expression data alone. This discovery step was followed by stringent validation, which included microdissection prior to PCR analyses to tackle the problem of stromal contamination. The availability of TMAs coupled with outcome data provided robust protein level validation and enabled investigation of the prognostic significance of gene targets. The mechanisms for protein over-expression were not examined, but the proportion of samples with genomic gains matched the proportion of samples with protein over-expression of EGFR, NEIL2 and MTMR9. In the case of WT1, amplification is not the only mechanism responsible for its over-expression in OACs. A limitation of the study is that this aCGH platform has been superseded by higher density arrays including SNP arrays which permit more detailed analysis of copy number changes. In order to overcome this, whole-genome SNP array analysis was carried out on samples of interest identified from aCGH analysis to validate our findings. Lastly, we demonstrated the potential of a prognostic aCGH signature on an independent dataset, but eventually larger sample cohorts would be needed to overcome the limitations of a small sample size and to reduce errors caused by inter-cohort variability.

Overall, these findings provide important insights into OAC pathogenesis with promising data to support their utility as prognostic biomarkers.

Future cancer management may be improved if our knowledge of the biology and genetics of cancers can be integrated with clinical applications.

REFERENCES TO EXAMPLE 3

1. Pohl H, Welch H G. The role of overdiagnosis and reclassification in the marked increase of esophageal adenocarcinoma incidence. *J Natl Cancer Inst* 2005; 97(2):142-6.

2. Mitry E, Ratchet B, Quinn M J, et al. Survival from cancer of the oesophagus in England and Wales up to 2001. *Br J Cancer* 2008; 99 Suppl 1:S11-3.
3. Solomon E, Borrow J, Goddard A D. Chromosome aberrations and cancer. *Science* 1991; 254(5035):1153-60.
4. Weir B A, Woo M S, Getz G, et al. Characterizing the cancer genome in lung adenocarcinoma. *Nature* 2007; 450 (7171):893-8.
5. Classon M, Harlow E. The retinoblastoma tumour suppressor in development and cancer. *Nat Rev Cancer* 2002; 2(12):910-7.
6. Gu J, Ajani J A, Hawk E T, et al. Genome-wide catalogue of chromosomal aberrations in barrett's esophagus and esophageal adenocarcinoma: a high-density single nucleotide polymorphism array analysis. *Cancer Prev Res (Phila)* 2010; 3(9):1176-86.
7. Vans A, Puolakkainen P, Savolainen H, et al. DNA copy number profiling in esophageal Barrett adenocarcinoma: comparison with gastric adenocarcinoma and esophageal squamous cell carcinoma. *Cancer Genet Cytogenet* 2001; 127(1):53-8.
8. Bang Y J, Van Cutsem E, Feyereislova A, et al. Trastuzumab in combination with chemotherapy versus chemotherapy alone for treatment of HER2-positive advanced gastric or gastro-oesophageal junction cancer (ToGA): a phase 3, open-label, randomised controlled trial. *Lancet* 2010; 376(9742):687-97.
9. Reid B J, Prevo L J, Galipeau P C, et al. Predictors of progression in Barrett's esophagus II: baseline 17p (p53) loss of heterozygosity identifies a patient subset at increased risk for neoplastic progression. *The American journal of gastroenterology* 2001; 96(10):2839-48.
10. Powell E L, Leoni L M, Canto M I, et al. Concordant loss of MTAP and p16/CDKN2A expression in gastroesophageal carcinogenesis: evidence of homozygous deletion in esophageal noninvasive precursor lesions and therapeutic implications. *Am J Surg Pathol* 2005; 29(11):1497-504.
11. Wong D J, Paulson T G, Prevo L J, et al. p16(INK4a) lesions are common, early abnormalities that undergo clonal expansion in Barrett's metaplastic epithelium. *Cancer Res* 2001; 61(22):8284-9.
12. Michael D, Beer D G, Wilke C W, et al. Frequent deletions of FHIT and FRA3B in Barrett's metaplasia and esophageal adenocarcinomas. *Oncogene* 1997; 15(14): 1653-9.
13. Wiech T, Nikolopoulos E, Weis R, et al. Genome-wide analysis of genetic alterations in Barrett's adenocarcinoma using single nucleotide polymorphism arrays. *Laboratory investigation; a journal of technical methods and pathology* 2009; 89(4):385-97.
14. Nancarrow D J, Handoko H Y, Smithers B M, et al. Genome-wide copy number analysis in esophageal adenocarcinoma using high-density single-nucleotide polymorphism arrays. *Cancer Res* 2008; 68(11):4163-72.
15. Kindler H L, Burris H A, 3rd, Sandler A B, Oliff I A. A phase II multicenter study of L-alanosine, a potent inhibitor of adenine biosynthesis, in patients with MTAP-deficient cancer. *Invest New Drugs* 2009; 27(1):75-81.
16. Snijders A M, Nowak N, Segraves R, et al. Assembly of microarrays for genome-wide measurement of DNA copy number. *Nat Genet* 2001; 29(3):263-4.
17. van den Ijssel P, Tijssen M, Chin S F, et al. Human and mouse oligonucleotide-based array CGH. *Nucleic Acids Res* 2005; 33(22):e192.
18. Peters C J, Rees J R, Hardwick R H, et al. A 4-gene signature predicts survival of patients with resected adenocarcinoma of the esophagus, junction, and gastric cardia. *Gastroenterology* 2010; 139(6):1995-2004 el 5.
19. Santarius T, Shipley J, Brewer D, et al. A census of amplified and overexpressed human cancer genes. *Nat Rev Cancer;* 10(1):59-64.
20. Schutze K, Lahr G. Identification of expressed genes by laser-mediated manipulation of single cells. *Nat Biotechnol* 1998; 16(8):737-42.
21. Caldon C E, Lee C S, Sutherland R L, et al. Wilms' tumor protein 1: an early target of progestin regulation in T-47D breast cancer cells that modulates proliferation and differentiation. *Oncogene* 2008; 27(1):126-38.
22. Chung-man Ho J, Zheng S, Comhair S A, et al. Differential expression of manganese superoxide dismutase and catalase in lung cancer. *Cancer Res* 2001; 61(23):8578-85.
23. Hill A, McFarlane S, Mulligan K, et al. Cortactin underpins CD44-promoted invasion and adhesion of breast cancer cells to bone marrow endothelial cells. *Oncogene* 2006; 25(45):6079-91.
24. Yamada H, Yanagisawa K, Tokumaru S, et al. Detailed characterization of a homozygously deleted region corresponding to a candidate tumor suppressor locus at 21q11-21 in human lung cancer. *Genes Chromosomes Cancer* 2008; 47(9):810-8.
25. Anders M, Vieth M, Rocken C, et al. Loss of the coxsackie and adenovirus receptor contributes to gastric cancer progression. *Br J Cancer* 2009; 100(2):352-9.
26. Fukuchi M, Nakajima M, Fukai Y, et al. Increased expression of c-Ski as a co-repressor in transforming growth factor-beta signaling correlates with progression of esophageal squamous cell carcinoma. *Int J Cancer* 2004; 108(6):818-24.
27. Parsons D W, Wang T L, Samuels Y, et al. Colorectal cancer: mutations in a signalling pathway. *Nature* 2005; 436(7052):792.
28. Ferby I, Reschke M, Kudlacek O, et al. Mig6 is a negative regulator of EGF receptor-mediated skin morphogenesis and tumor formation. *Nature medicine* 2006; 12(5):568-73.
29. Takeda K, Kinoshita I, Shimizu Y, et al. Clinicopathological significance of expression of p-c-Jun, TCF4 and beta-Catenin in colorectal tumors. *BMC Cancer* 2008; 8:328.
30. Kim R H, Peters M, Jang Y, et al. DJ-1, a novel regulator of the tumor suppressor PTEN. *Cancer cell* 2005; 7(3): 263-73.
31. Pasello G, Agata S, Bonaldi L, et al. DNA copy number alterations correlate with survival of esophageal adenocarcinoma patients. *Mod Pathol* 2009; 22(1):58-65.
32. Ginestier C, Charafe-Jauffret E, Penault-Llorca F, et al. Comparative multi-methodological measurement of ERBB2 status in breast cancer. *J Pathol* 2004; 202(3): 286-98.
33. Wang K L, Wu T T, Choi I S, et al. Expression of epidermal growth factor receptor in esophageal and esophagogastric junction adenocarcinomas: association with poor outcome. *Cancer* 2007; 109(4):658-67.
34. Niksic M, Slight J, Sanford J R, et al. The Wilms' tumour protein (WT1) shuttles between nucleus and cytoplasm and is present in functional polysomes. *Hum Mol Genet* 2004; 13(4):463-71.
35. Han Y, San-Marina S, Liu J, et al. Transcriptional activation of c-myc proto-oncogene by WT1 protein. *Oncogene* 2004; 23(41):6933-41.

36. Fraizer G, Leahy R, Priyadarshini S, et al. Suppression of prostate tumor cell growth in vivo by WT1, the Wilms' tumor suppressor gene. *Int J Oncol* 2004; 24(3):461-71.
37. Gross I, Morrison D J, Hyink D P, et al. The receptor tyrosine kinase regulator Sproutyl is a target of the tumor suppressor WT1 and important for kidney development. *J Biol Chem* 2003; 278(42):41420-30.
38. Lee S B, Huang K, Palmer R, et al. The Wilms tumor suppressor WT1 encodes a transcriptional activator of amphiregulin. *Cell* 1999; 98(5):663-73.
39. Rodriguez E, Rao P H, Ladanyi M, et al. 11p13-15 is a specific region of chromosomal rearrangement in gastric and esophageal adenocarcinomas. *Cancer Res* 1990; 50(19):6410-6.
40. Hazra T K, Izumi T, Boldogh I, et al. Identification and characterization of a human DNA glycosylase for repair of modified bases in oxidatively damaged DNA. *Proc Natl Acad Sci* USA 2002; 99(6):3523-8.
41. Mochizuki Y, Majerus P W. Characterization of myotubularin-related protein 7 and its binding partner, myotubularin-related protein 9. *Proc Natl Aced Sci USA* 2003; 100(17):9768-73
42. Zou J, Chang S C, Marjanovic J, et al. MTMR9 increases MTMR6 enzyme activity, stability, and role in apoptosis. *J Biol Chem* 2009; 284(4):2064-71.
43. Schoorlemmer J, Goldfarb M. Fibroblast growth factor homologous factors and the islet brain-2 scaffold protein regulate activation of a stress-activated protein kinase. *J Biol Chem* 2002; 277(51):49111-9.
44. Vantaggiato C, Redaelli F, Falcone S, et al. A novel CLN8 mutation in late-infantile-onset neuronal ceroid lipofuscinosis (LINCL) reveals aspects of CLN8 neurobiological function. *Human mutation* 2009; 30(7):1104-16.

Example 4

Method of Aiding Prognosis

We demonstrate that a combination of gene expression profiling and array-comparative genomic hybridisation analysis generates an improved prognostic model for oesophageal adenocarcinoma.
Background
We have described above a 4 gene signature that can divide patients with oesophageal adenocarcinma into 3 prognostic groups. The 4 genes included in the gene signature are SIRT2, TRIM44, DCK and PAPS2. This has been validated on an independent set of patient samples.

We have also been keen to see whether we can improve upon this molecular prognostic signature. For example, DCK has borderline significance and for example a majority of patients fall into the intermediate prognosis group.

Using array-comparative genomic hybridisation (aCGH) analysis on 56 fresh frozen OAC resection samples, from the same sample set used for expression profiling with long-term clinical follow-up data, we have identified 4 targets with high copy number-expression correlations (EGFR, WT1, NEIL2, MTMR9). Immunohistochemistry confirmed protein over-expression of targets with gains: EGFR (10%), WT1 (20%), NEIL2 (14%) and MTMR9 (25%). These targets individually (p<0.060) and in combination had prognostic significance (p=0.008). This is described in more detail in the previous example.

To determine the optimal combination of genes that can prognosticate patients with oesophageal cancer, we analysed the hazard ratios of each of these 8 over-expressed proteins (SIRT2, TRIM44, DCK. PAPS2, EGFR, WT1, NEIL2, MTMR9) in a cohort of 314 patients using a cox regression model. This analysis is based on a binary score of 0 (underexpression) and 1 (overexpression) for all targets. Table SA8 shows the results of the analysis with the genes ranked according to the hazard ratio:

TABLE SA8

Survival analysis for the 8 genes

| | Age, sex adjusted | P |
|---|---|---|
| TRIM44 | | |
| Not Dysregulated | Reference | 0.001 |
| Dysregulated | 1.64 (1.21-2.23) | |
| SIRT2 | | |
| Not Dysregulated | Reference | 0.051 |
| Dysregulated | 1.34 (1.00-1.80) | |
| WT1 | | |
| Not Dysregulated | 1.32 (0.94-1.86) | 0.114 |
| Dysregulated | Reference | |
| EGFR | | |
| Not Dysregulated | Reference | 0.294 |
| Dysregulated | 1.26 (0.82-1.92) | |
| PAPPS2 | | |
| Not Dysregulated | Reference | 0.215 |
| Dysregulated | 1.20 (0.90-1.59) | |
| DCK | | |
| Not Dysregulated | Reference | 0.573 |
| Dysregulated | 1.09 (0.82-1.45) | |
| MTMR9 | | |
| Not Dysregulated | Reference | 0.696 |
| Dysregulated | 1.07 (0.77-1.47) | |
| NEIL2 | | |
| Not Dysregulated | Reference | 0.982 |
| Dysregulated | 1.00 (0.77-1.31) | |

Using the cox regression model, we have determined that TRIM44, SIRT2, WT1, EGFR and PAPS2 have the most significant impact on a patient's survival. DCK, MTMR9 and NEIL2 had borderline impact on the hazard ratio of patients.

This analysis has provided greater insight on the contribution of each gene in predicting the prognosis of patients with oesophageal cancer.

This especially useful signature may be validated in an independent large cohort of patients with oesophageal adenocarcinoma. Paraffin samples from tumour specimens are stained for all 8 targets: that TRIM44, SIRT2, WT1, EGFR, PAPS2, DCK, MTMR9 and NEIL2. This enables validation of the new hybrid gene signature. This enables comparison to, and to determine if it outperforms, the 4 gene signature SIRT2, TRIM44, DCK and PAPS2. The skilled worker may choose which signature(s) to use.
Additional Prognostic Modelling A Cox Hazard Proportional Model led to the determination of 4 candidate genes with significant hazard ratios or hazard ratios which approached significance: TRIM44, SIRT2 (from the 4 gene signature first described above) and WT1 and EGFR (from the aCGH analysis).

In addition, we found age was another significant risk factor in determining prognosis and was hence taken into account in the prediction model. During the sensitivity analysis, we discovered that there is a possible interaction between these genes and we derived a model to calculate a risk score for each patient to discriminate different prognosis. The formula is as follows: Risk=0.017*AGE+0.800*TRIM44+0.567*SIRT2−0.019*Wt1_ave+0.627*EGFR−0.818*SIRT2*EGFR−0.358*TRIM44*SIRT2-0.415*TRIM44*EGFR+1.082*EGFR*Wt1−0.684*Wt1*TRIM44.

Figure 7:
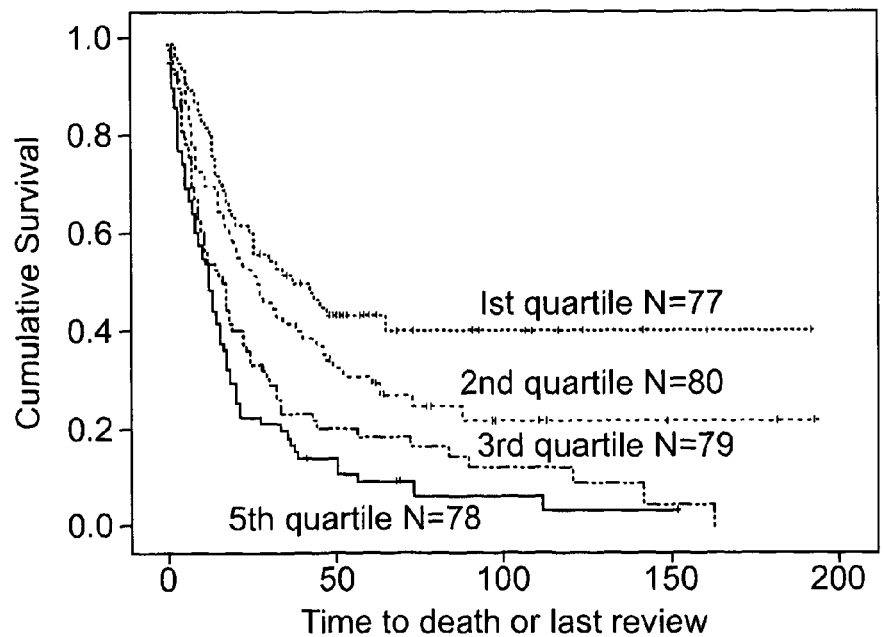
FIG. 7 shows Kaplan-Meier survival curves.

Using this four gene algorithm combined with age, patients were divided into 4 prognostic groups by quartiles of the risk score. The Kaplan-Meier survival curves are shown in FIG. 7 according to quartiles of risk score (Log-rank test: P<0.01).

This signature has the advantage of greater prognostic power than the original 4 gene signature SIRT2, TRIM44, DCK and PAPS2. In addition, patients are more equally divided between the groups, which can also be advantageous.

TABLE 1

List of biomarkers with their associated accession numbers

| Biomarker | Accession Number |
| --- | --- |
| UBE2D2 | NM_181838 |
| NEDD9 (HEF1) | NM_006403 |
| TRIM44 | NM_017583 |
| DCK | NM_000788 |
| PAPSS2 | HSS00023134 |
| MNT | NM_020310 |
| PLK1 | HSS00056704 |
| NEU4 | NM_080741 |
| C5AR1 | NM_001736 |
| ADCY9 | NM_001116 |
| UNC93B1 | NM_030930 |
| SIRT2 | NM_012237 |
| LPHN3 | AK094703 |
| EFCBP1 | NM_022351 |
| TSPAN5 | NM_005723 |
| TREM2 | NM_018965 |
| ITGB6 | AL359053 |
| ARTS-1 | NM_016442 |
| TCF15 | NM_004609 |
| FGD2 | NM_173558 |
| WT1 | NM_000378.4 |
| EGFR | NM_005228.3 |
| Neil2 | NM_001135748.1 |
| MTMR9 | NM_015458.3 |

An exemplary TRIM 44 sequence is Swiss-Prot Q96DX7 (SEQ ID NO.17):

```
          10         20         30         40         50         60
  MASGVGAAFE ELPHDGTCDE CEPDEAPGAE EVCRECGFCY CRRHAEAHRQ KFLSHHLAEY 70         80         90        100        110        120
  VHGSQAWTPP ADGEGAGKEE AEVKVEQERE IESEAGEESE SEEESESEEE SETEEESEDE 130        140        150        160        170        180
  SDEESEEDSE EEMEDEQESE AEEDNQEEGE SEAEGETEAE SEFDPEIEME AERVAKRKCP 190        200        210        220        230        240
  DHGLDLSTYC QEDRQLICVL CPVIGAHQGH QLSTLDEAFE ELRSKDSGGL KAAMIELVER 250        260        270        280        290        300
  LKFKSSDPKV TRDQMKMFIQ QEFKKVQKVI ADEEQKALHL VDIQEAMATA HVTEILADIQ 310        320        330        340
  SHMDRLMTQM AQAKEQLDTS NESAEPKAEG DEEGPSGASE EEDT
```

An exemplary PAPSS2 sequence is Swiss-Prot O95340 (SEQ ID NO.18):

```
          10         20         30         40         50         60
  MSGIKKQKTE NQQKSTNVVY QAHHVSRNKR GQVVGTRGGF RGCTVWLTGL SGAGKTTISF 70         80         90        100        110        120
  ALEEYLVSHA IPCYSLDGDN VRHGLNRNLG FSPGDREENI RRIAEVAKLF ADAGLVCITS 130        140        150        160        170        180
  FISPFAKDRE NARKIHESAG LPFFEIFVDA PLNICESRDV KGLYKRARAG EIKGFTGIDS 190        200        210        220        230        240
  DYEKPETPER VLKTNLSTVS DCVHQVVELL QEQNIVPYTI IKDIHELFVP ENKLDHVRAE 250        260        270        280        290        300
  AETLPSLSIT KLDLQWVQVL SRGWATPLKG FMREKEYLQV MHFDTLLDDG VINMSIPIVL 310        320        330        340        350        360
  PVSAEDKTRL EGCSKFVLAH GGRRVAILRD AEFYEHRKEE RCSRVWGTTC TKHPHIKNVM 370        380        390        400        410        420
  ESGDWLVGGD LQVLEKIRWN DGLDQYRLTP LELKQKCKEM NADAVFAFQL RNPVHNGHAL 430        440        450        460        470        480
  LMQDTRRRLL ERGYKHPVLL LHPLGGWTKD DDVPLDWRMK QHAAVLEEGV LDPKSTIVAI
```

-continued

```
        490         500         510         520         530         540
FPSPMLYAGP  TEVQWHCRSR  MIAGANFYIV  GRDPAGMPHP  ETKKDLYEPT  HGGKVLSMAP 550         560         570         580         590         600
GLTSVEIIPF  RVAAYNKAKK  AMDFYDPARH  NEFDFISGTR  MRKLAREGEN  PPDGFMAPKA

610
WKVLTDYYRS  LEKN
```

An exemplary SIRT2 sequence is Swiss-Prot Q8IXJ6 (SEQ ID NO.19):

```
         10          20          30          40          50          60
MAEPDPSHPL  ETQAGKVQEA  QDSDSDSEGG  AAGGEADMDF  LRNLFSQTLS  LGSQKERLLD 70          80          90         100         110         120
ELTLEGVARY  MQSERCRRVI  CLVGAGISTS  AGIPDFRSPS  TGLYDNLEKY  HLPYPEAIFE 130         140         150         160         170         180
ISYFKKHPEP  FFALAKELYP  GQFKPTICHY  FMRLLKDKGL  LLRCYTQNID  TLERIAGLEQ 190         200         210         220         230         240
EDLVEAHGTF  YTSHCVSASC  RHEYPLSWMK  EKIFSEVTPK  CEDCQSLVKP  DIVFFGESLP 250         260         270         280         290         300
ARFFSCMQSD  FLKVDLLLVM  GTSLQVQPFA  SLISKAPLST  PRLLINKEKA  GQSDPFLGMI 310         320         330         340         350         360
MGLGGGMDFD  SKKAYRDVAW  LGECDQGCLA  LAELLGWKKE  LEDLVRREHA  SIDAQSGAGV 370         380
PNPSTSASPK  KSPPPAKDEA  RTTEREKPQ
```

An exemplary DCK sequence is Swiss-Prot P27707-1 (SEQ ID NO.20):

```
         10          20          30          40          50          60
MATPPKRSCP  SFSASSEGTR  IKKISIEGNI  AAGKSTFVNI  LKQLCEDWEV  VPEPVARWCH 70          80          90         100         110         120
VQSTQDEFEE  LTMSQKNGGN  VLQMMYEKPE  RWSFTFQTYA  CLSRIRAQLA  SLNGKLKDAE 130         140         150         160         170         180
KPVLFFERSV  YSDRYIFASN  LYESECMNET  EWTIYQDWHD  WMNNQFGQSL  ELDGIIYLQA 190         200         210         220         230         240
TPETCLHRIY  LRGRNEEQGI  PLEYLEKLHY  KHESWLLHRT  LKTNFDYLQE  VPILTLDVNE 250         260
DFKDKYESLV  EKVKEFLSTL
```

An exemplary WT1 sequence is RefSeq: NM_000378.4 (SEQ ID NO.21):

MQDPASTCVPEPASQHTLRSGPGCLQQPEQQGVRDPGGIWAKLG

AAEASAERLQGRRSRGASGSEPQQMGSDVRDLNALLPAVPSLGGGGGCA

LPVSGAAQWAPVLDFAPPGASAYGSLGGPAPPPAPPPPPPPPHSFIKQ

EPSWGGAEPHEEQCLSAFTVHFSGQFTGTAGACRYGPFGPPPPSQASSG

QARMFPNAPYLPSCLESQPAIRNQGYSTVTFDGTPSYGHTPSHHAAQFP

NHSFKHEDPMGQQGSLGEQQYSVPPPVYGCHTPTDSCTGSQALLLRTPY

SSDNLYQMTSQLECMTWNQMNLGATLKGHSTGYESDNHTTPILCGAQYR

IHTHGVFRGIQDVRRVPGVAPTLVRSASETSEKRPFMCAYPGCNKRYFK

LSHLQMHSRKHTGEKPYQCDFKDCERRFSRSDQLKRHQRRHTGVKPFQC

KTCQRKFSRSDHLKTHTRTHTGEKPFSCRWPSCQKKFARSDELVRHHNM

HQRNMTKLQLAL

An exemplary EGFR sequence is RefSeq: NM_005228.3 (SEQ ID NO.22):

MRPSGTAGAALLALLAALCPASRALEEKKVCQGTSNKLTQLGTF

EDHFLSLQRMFNNCEVVLGNLEITYVQRNYDLSFLKTIQEVAGYVLIAL

NTVERIPLENLQIIRGNMYYENSYALAVLSNYDANKTGLKELPMRNLQE

ILHGAVRFSNNPALCNVESIQWRDIVSSDFLSNMSMDFQNHLGSCQKCD

PSCPNGSCWGAGEENCQKLTKIICAQQCSGRCRGKSPSDCCHNQCAAGC

TGPRESDCLVCRKFRDEATCKDTCPPLMLYNPTTYQMDVNPEGKYSFGA

TCVKKCPRNYVVTDHGSCVRACGADSYEMEEDGVRKCKKCEGPCRKVCN

GIGIGEFKDSLSINATNIKHFKNCTSISGDLHILPVAFRGDSFTHTPPL

DPQELDILKTVKEITGFLLIQAWPENRTDLHAFENLEIIRGRTKQHGQF

SLAVVSLNITSLGLRSLKEISDGDVIISGNKNLCYANTINWKKLFGTSG

-continued
QKTKIISNRGENSCKATGQVCHALCSPEGCWGPEPRDCVSCRNVSRGRE

CVDKCNLLEGEPREFVENSECIQCHPECLPQAMNITCTGRGPDNCIQCA

HYIDGPHCVKTCPAGVMGENNTLVWKYADAGHVCHLCHPNCTYGCTGPG

PLEGCPTNGPKIPSIATGMVGALLLLLVVALGIGLFMRRRHIVRKRTLR

RLLQERELVEPLTPSGEAPNQALLRILKETEFKKIKVLGSGAFGTVYKG

LWIPEGEKVKIVAIKELREATSPKANKEILDEAYVMASVDNPHVCRLLG

ICLTSTVQLITQLMPFGCLLDYVREHKDNIGSQYLLNWCVQIAKGMNYL

EDRRLVHRDLAARNVLVKTPQHVKITDFGLAKLLGAEEKEYHAEGGKVP

IKWMALESILHRIYTHQSDVWSYGVTVWELMTFGSKPYDGIPASEISSI

LEKGERLPQPPICTIDVYMIMVKCWMIDADSRPKFRELIIEFSKMARDP

QRYLVIQGDERMHLPSPTDSNFYRALMDEEDMDDVVDADEYLIPQQGFF

SSPSTSRTPLLSSLSATSNNSTVACIDRNGLQSCPIKEDSFLQRYSSDP

TGALTEDSIDDTFLPVPEYINQSVPKRPAGSVQNPVYHNQPLNPAPSRD

PHYQDPHSTAVGNPEYLNTVQPTCVNSTFDSPAHWAQKGSHQISLDNPD

YQQDFFPKEAKPNGIFKGSTAENAEYLRVAPQSSEFIGA

An exemplary NEIL2 sequence is RefSeq: NM_001135748.1 (SEQ ID NO.23):

MPEGPLVRKFHHLVSPFVGQQVVKTGGSSKKLQPASLQSLWLQD

TQVRLVLHFGGGGFLAFYNCQLSWSSSPVVTPTCDILSEKFHRGQALEA

LGQAQPVCYTLLDQRYFSGLGNIIKNEALYRAGIHPLSLGSVLSASRRE

VLVDHVVEFSTAWLQGKFQGRPQHTQVYQKEQCPAGHQVMKEAFGPEDG

LQRLTWWCPQCQPQLSEEPEQCQFS

An exemplary MTMR9 sequence is RefSeq: NM_015458.3 (SEQ ID NO.24):

MEFAELIKTPRVDNVVLHRPFYPAVEGTLCLTGHHLILSSRQDN

TEELWLLHSNIDAIDKRFVGSLGTIIIKCKDFRIIQLDIPGMEECLNIA

SSIEALSTLDSITLMYPFFYRPMFEVIEDGWHSFLPEQEFELYSSATSE

WRLSYVNKEFAVCPSYPPIVTVPKSIDDEALRKVATFRHGGRFPVLSYY

HKKNGMVIMRSGQPLTGTNGRRCKEDEKLINATLRAGKRGYIIDTRSLN

VAQQTRAKGGGFEQEAHYPQWRRIHKSIERYHILQESLIKLVEACNDQT

HNMDRWLSKLEASNWLTHIKEILTTACLAAQCIDREGASILIHGTEGTD

STLQVTSLAQIILEPRSRTIRGFEALIEREWLQAGHPFQQRCAQSAYCN

TKQKWEAPVFLLFLDCVWQILRQFPCSFEFNENFLIMLFEHAYASQFGT

FLGNNESERCKLKLQQKTMSLWSWVNQPSELSKFTNPLFEANNLVIWPS

VAPQSLPLWEGIFLRWNRSSKYLDEAYEEMVNIIEYNKELQAKVNILRR

QLAELETEDGMQESP

TABLE 2

Clinical and pathological characteristics of the patients included in the generation and validation datasets. Comparisons between groups carried out using the $\chi^2$ test unless indicated otherwise ‡Mann-Whitney U test

| | | Generation Dataset (n = 75) | | Validation dataset (n = 371) | | Test Statistic | Degrees of Freedom | P |
|---|---|---|---|---|---|---|---|---|
| | | Number | % | Number | % | | | |
| Sex | Male | 47 | 62 | 296 | 80 | $\chi^{2L}$ = 9.07 | 1 | 0.0026 |
| | Female | 28 | 37 | 76 | 20 | | | |
| Median Age | | 67 | Range 35-81 | 66 | Range 29-88 | U = 7798 | | 0.733 § |
| Siewert Classification | Type I/ Esophageal | 36 | 47 | 260 | 70 | $\chi^{2L}$ = 24.3 | 3 | <0.0001 |
| | Type II/ Junctional | 8 | 11 | 34 | 9 | | | |
| | Type III/ Gastric | 19 | 25 | 64 | 17 | | | |
| | Unknown | 12 | 17 | 13 | 4 | | | |
| Chemotherapy | Yes | 4 | 5 | 143 | 39 | $\chi^{2L}$ = 81.41 | 2 | <0.0001 |
| | No | 71 | 93 | 140 | 38 | | | |
| | Unknown | 0 | 0 | 88 | 24 | | | |
| Differentiation | Well | 7 | 9 | 26 | 7 | $\chi^{2L}$ = 24.51 | 3 | <0.0001 |
| | Moderate | 31 | 41 | 90 | 24 | | | |
| | Poor | 37 | 49 | 184 | 50 | | | |
| | Unknown | 0 | 0 | 71 | 19 | | | |
| T-stage | T1 | 5 | 7 | 24 | 7 | $\chi^{2L}$ = 6.63 | 4 | 0.16 |
| | T2 | 17 | 23 | 49 | 13 | | | |
| | T3 | 39 | 52 | 225 | 61 | | | |
| | T4 | 1 | 1 | 18 | 5 | | | |
| | Unknown | 13 | 17 | 55 | 15 | | | |
| N-stage | N0 | 14 | 19 | 94 | 25 | $\chi^{2L}$ = 1.58 | 2 | 0.45 |
| | N1 | 48 | 64 | 222 | 60 | | | |
| | Unknown | 13 | 17 | 55 | 15 | | | |
| M-Stage | M0 | 59 | 78 | 270 | 73 | $\chi^{2L}$ = 1.25 | 2 | 0.54 |
| | M1 | 3 | 4 | 15 | 4 | | | |
| | Unknown | 13 | 17 | 86 | 23 | | | |
| Median follow up | All patients | 20 months | Range 0.5-137 | 17 months | Range 0.5-193 | U = 10817 | | 0.30 § |
| | Survivors | 89 months | Range 66-137 | 57 months | Range 12-137 | U = 282 | | 0.001 § |

TABLE 3

A list of the sources for antibodies used in the study
and the conditions used for optimum staining.

| Target | Product Number | Antibody Source | BOND Immunohistochemistry Conditions |
|---|---|---|---|
| C5AR1 | Ab12962 | Abcam Plc, 232 Cambridge Science Park, Cambridge, CB4 0FW, UK. | 1/300+12 Dilution IHC protocol F + DAB Enhancer HIER Epitope Retrieval Solution 2 for 30 minutes |
| PLK-1 | PAB2309 | Abnova GmbH c/o EMBLEM Boxbergring 107 69126 Heidelberg Germany. | 1/25 Dilution IHC protocol F + DAB Enhancer HIER Epitope Retrieval Solution 2 for 30 minutes |
| MNT | Ab53487 | Abcam Plc, 232 Cambridge Science Park, Cambridge, CB4 0FW, UK. | 1/10 Dilution IHC protocol F + DAB Enhancer HIER Epitope Retrieval Solution 2 for 30 minutes |
| DCK | LS-B1852/ 16035 | LifeSpan Biosciences, Inc. 2401 Fourth Avenue Suite 900, Seattle, WA 98121, USA. | 1/10 Dilution IHC protocol F + DAB Enhancer HIER Epitope Retrieval Solution 2 for 30 minutes |
| PAPSS2 | Ab56393 | Abcam Plc, 232 Cambridge Science Park, Cambridge, CB4 0FW, UK. | 1/600 Dilution IHC protocol F + DAB Enhancer HIER Epitope Retrieval Solution 1 for 30 minutes |
| SIRT2 | HPA011165 | Atlas Antibodies AB, Albanova University Center, SE 106 91, Stockholm, Sweden. | 1/100 Dilution IHC protocol F HIER Epitope Retrieval Solution 2 for 30 minutes |
| TRIM44 | 11511-1-AP | ProteinTech Group, Inc. 2201 W. Campbell Park Dr. Chicago, IL, 60612, USA. | 1/50 Dilution IHC protocol F + DAB Enhancer HIER Epitope Retrieval Solution 1 for 30 minutes |
| UBE2D2 | H00007322-M02 | Abnova GmbH c/o EMBLEM Boxbergring 107 69126 Heidelberg Germany. | 1/200 Dilution IHC protocol F + DAB Enhancer HIER Epitope Retrieval Solution 1 for 30 minutes |

TABLE 4

Median survial with 95% confidence interval of patients in the internal
validation dataset with and without dysregulation of DCK, PAPSS2, SIRT2,
and TRIM44. P-values calculated using the log rank (Mantel-Cox) test.

| Target | Median Survival if dysregulated | Median Survival if not dysregulated | Test Statistic | Degrees of Freedom | P-value |
|---|---|---|---|---|---|
| DCK | 9.9 months (95% CI 5.0-14.8) | 18.2 months (95% CI 0.6-35.7) | $\chi_v^2 = 4.46$ | 1 | 0.035 |
| PAPSS2 | 7.8 months (95% CI 5.5-10.1) | 31.2 months (95% CI 0-64.5) | $\chi_v^2 = 12.11$ | 1 | 0.001 |
| SIRT2 | 17.0 months (95% CI 8.6-25.4) | 25.0 months (95% CI 0.0-63.3) | $\chi_v^2 = 3.97$ | 1 | 0.046 |
| TRIM44 | 11.6 months (95% CIl 1.8-21.3) | 27.2 months (95% CI 13.3-41.1) | $\chi_v^2 = 3.35$ | 1 | 0.063 |

TABLE 5

Backwards stepwise Cox regression with differentiation, existing TNM system,
neurovascular invasion, resection margin status and the four gene TRIM44,
SIRT2, PAPPS2 and DCK signature entered into the model. The T-stage,
N-stage and the four gene signature remain in the final model (Step 5)

| | Feature | Comparison | Significance | Hazard Ratio | 95.0% CI for Hazard Ratio Lower | Upper |
|---|---|---|---|---|---|---|
| Step 1 | Differentiation | Overall | 0.546 | | | |
| | | Moderate y v Well | 0.968 | 0.986 | 0.490 | 1.984 |
| | | Poorly v Well | 0.496 | 1.296 | 0.652 | 2.421 |
| | T-stage | Overall | 0.005 | | | |
| | | T2 v T1 | 0.176 | 2.467 | 0.666 | 9.139 |
| | | T3 v T1 | 0.283 | 3.077 | 0.865 | 10.945 |
| | | T4 v T1 | 0.801 | 17.136 | 3.159 | 92.978 |
| | N-stage | N1 v N0 | 0.001 | 2.973 | 1.573 | 5.621 |
| | M-stage | M1 v M0 | 0.642 | 0.713 | 0.172 | 2.960 |
| | Neurovascular Invasion | Invasion v None | 0.578 | 1.140 | 0.718 | 1.809 |
| | Resection margin status | R1 v R0 | 0.786 | 1.065 | 0.676 | 1.673 |
| | 3 Gene Signature | Overall | 0.006 | | | |
| | | 1/3 v 0/3 Genes Dysregulated | 0.016 | 3.018 | 1.225 | 7.435 |
| | | 2-3/3 v 0/3 Genes Dysregulated | 0.002 | 4.131 | 1.699 | 10.045 |
| Step 2 | Differentiation | Overall | 0.946 | | | |
| | | Moderate y v Well | 0.940 | 0.974 | 0.486 | 1.948 |
| | | Poorly v Well | 0.511 | 1.244 | 0.648 | 2.390 |
| | T-stage | Overall | 0.002 | | | |
| | | T2 v T1 | 0.168 | 2.505 | 0.679 | 9.235 |
| | | T3 v T1 | 0.071 | 3.169 | 0.908 | 11.068 |
| | | T4 v T1 | 0.001 | 18.193 | 3.549 | 93.254 |
| | N-stage | N1 v N0 | 0.001 | 2.979 | 1.575 | 5.632 |
| | M-stage | M1 v M0 | 0.653 | 0.722 | 0.174 | 2.986 |
| | Neurovascular Invasion | Invasion v None | 0.572 | 1.143 | 0.720 | 1.813 |
| | 3 Gene Signature | Overall | 0.005 | | | |
| | | 1/3 v 0/3 Genes Dysregulated | 0.016 | 3.034 | 1.232 | 7.469 |
| | | 2-3/3 v 0/3 Genes Dysregulated | 0.001 | 4.196 | 1.737 | 10.136 |
| Step 3 | Differentiation | Overall | 0.544 | | | |
| | | Moderate y v Well | 0.945 | 0.976 | 0.488 | 1.952 |
| | | Poorly v Well | 0.506 | 1.248 | 0.650 | 2.396 |
| | T-stage | Overall | 0.002 | | | |
| | | T2 v T1 | 0.165 | 2.517 | 0.683 | 9.275 |
| | | T3 v T1 | 0.071 | 3.161 | 0.905 | 11.042 |
| | | T4 v T1 | 0.000 | 18.336 | 3.577 | 93.985 |
| | N-stage | N1 v N0 | 0.001 | 2.987 | 1.568 | 5.613 |
| | Neurovascular Invasion | Invasion v None | 0.604 | 1.129 | 0.713 | 1.789 |
| | 3 Gene Signature | Overall | 0.205 | | | |
| | | 1/3 v 0/3 Genes Dysregulated | 0.017 | 2.987 | 1.215 | 7.341 |
| | | 2-3/3 v 0/3 Genes Dysregulated | 0.001 | 4.175 | 1.729 | 10.083 |

Backwards stepwise Cox regression with differentiation, existing TNM system,
neurovascular invasion, resection margin status and the four gene TRIM44,
SIRT2, PAPPS2 and DCK signature entered into the model. The T-stage,
N-stage and the four gene TRIM44, SIRT2, PAPPS2 and DCK signature
remain in the final model (Step 5)

| | Feature | Comparison | Significance | Hazard Ratio | Lower | Upper |
|---|---|---|---|---|---|---|
| Step 4 | Differentiation | Overall | 0.505 | | | |
| | | Moderate y v Well | 0.992 | 1.003 | 0.506 | 1.989 |
| | | Poorly v Well | 0.436 | 1.290 | 0.679 | 2.449 |
| | T-stage | Overall | 0.002 | | | |
| | | T2 v T1 | 0.163 | 2.529 | 0.686 | 9.318 |
| | | T3 v T1 | 0.060 | 3.294 | 0.952 | 11.394 |
| | | T4 v T1 | 0.001 | 18.037 | 3.524 | 92.334 |
| | N-stage | N1 v N0 | 0.001 | 3.011 | 1.593 | 5.690 |
| | 3 Gene Signature | Overall | 0.005 | | | |
| | | 1/3 v 0/3 Genes Dysregulated | 0.020 | 2.891 | 1.185 | 7.001 |
| | | 2-3/3 v 0/3 Genes Dysregulated | 0.002 | 4.110 | 1.708 | 9.893 |
| Step 5 | T-stage | Overall | 0.001 | | | |
| | | T2 v T1 | 0.099 | 2.862 | 0.821 | 9.974 |
| | | T3 v T1 | 0.035 | 3.628 | 1.094 | 12.027 |
| | | T4 v T1 | 0.000 | 21.188 | 4.358 | 103.008 |
| | N-stage | N1 v N0 | 0.001 | 3.042 | 1.613 | 5.735 |
| | 3 Gene Signature | Overall | 0.003 | | | |
| | | 1/3 v 0/3 Genes Dysregulated | 0.010 | 3.110 | 1.309 | 7.388 |
| | | 2-3/3 v 0/3 Genes Dysregulated | 0.001 | 4.321 | 1.816 | 10.282 |

REFERENCES

1. Cancer Stats. Cancer Research UK 2009:Available from: URL:http://info.cancerresearchuk.org/cancerstats/.
2. Allum W H, Stenning S P, Bancewicz J, Clark P I, Langley R E. Long-term results of a randomized trial of surgery with or without preoperative chemotherapy in esophageal cancer. J Clin Oncol 2009; 27:5062-7.
3. Sobin I, (editors) C W. TNM Classification of malignant tumours (6th Edition). John Wiley and Sons Inc, 2002.
4. van't Veer L J, Dai H, van de Vijver M J, He Y D, Hart A A, Mao M, Peterse H L, van der Kooy K, Marton M J, Witteveen A T, Schreiber G J, Kerkhoven R M, Roberts C, Linsley P S, Bernards R, Friend S H. Gene expression profiling predicts clinical outcome of breast cancer. Nature 2002; 415:530-6.
5. Paik S, Shak S, Tang G, Kim C, Baker J, Cronin M, Baehner F L, Walker M G, Watson D, Park T, Hiller W, Fisher E R, Wickerham D L, Bryant J, Wolmark N. A multigene assay to predict recurrence of tamoxifen-treated, node-negative breast cancer. N Engl J Med 2004; 351:2817-26.
6. Strayer M E, Glas A M, Hannemann J, Wesseling J, van de Vijver M J, Rutgers E J, Vrancken Peeters M J, van Tinteren H, Van't Veer L J, Rodenhuis S. The 70-gene signature as a response predictor for neoadjuvant chemotherapy in breast cancer. Breast Cancer Res Treat 2009.
7. van de Vijver M J, He Y D, van't Veer L J, Dai H, Hart A A, Voskuil D W, Schreiber G J, Peterse J L, Roberts C, Marton M J, Parrish M, Atsma D, Witteveen A, Glas A, Delahaye L, van der Velde T, Bartelink H, Rodenhuis S, Rutgers E T, Friend S H, Bernards R. A gene-expression signature as a predictor of survival in breast cancer. N Engl J Med 2002; 347:1999-2009.
8. Fan C, Oh D S, Wessels L, Weigelt B, Nuyten D S, Nobel A B, van't Veer L J, Perou C M. Concordance among gene-expression-based predictors for breast cancer. N Engl J Med 2006; 355:560-9.
9. Benowitz S. Revised guidelines signal that gene expression profiles are coming of age. J Natl Cancer Inst 2008; 100:916-7.
10. Ludwig J A, Weinstein J N. Biomarkers in cancer staging, prognosis and treatment selection. Nat Rev Cancer 2005; 5:845-56.
11. Pepe M S, Etzioni R, Feng Z, Potter J D, Thompson M L, Thornquist M, Winget M, Yasui Y. Phases of biomarker development for early detection of cancer. J Natl Cancer Inst 2001; 93:1054-61.
12. Barker P E. Cancer biomarker validation: standards and process: roles for the National Institute of Standards and Technology (NIST). Ann N Y Acad Sci 2003; 983:142-50.
13. Moons K G, Royston P, Vergouwe Y, Grobbee D E, Altman D G. Prognosis and prognostic research: what, why, and how? BMJ 2009; 338:b375.
14. Royston P, Moons K G, Altman D G, Vergouwe Y. Prognosis and prognostic research: Developing a prognostic model. BMJ 2009; 338:b604.
15. Altman D G, Vergouwe Y, Royston P, Moons K G. Prognosis and prognostic research: validating a prognostic model. BMJ 2009:338:b605.
16. Moons K G, Altman D G, Vergouwe Y, Royston P. Prognosis and prognostic research: application and impact of prognostic models in clinical practice. BMJ 2009:338:b606.
17. McShane L M, Altman D G, Sauerbrei W, Taube S E, Gion M, Clark G M. REporting recommendations for tumour MARKer prognostic studies (REMARK). Br J Cancer 2005; 93:387-91.
18. Peters C J, Hardwick R H, Vowler S L, Fitzgerald R C. Generation and validation of a revised classification for oesophageal and junctional adenocarcinoma. Br J Surg 2009; 96:724-33.
19. Korst R J, Rusch V W, Venkatraman E, Bains M S, Burt M E, Downey R J, Ginsberg R J. Proposed revision of the staging classification for esophageal cancer. J Thorac Cardiovasc Surg 1998; 115:660-69.
20. Pedrazzani C, de Manzoni G, Marrelli D, Giacopuzzi S, Corso G, Bernini M, Roviello F. Nodal Staging in Adenocarcinoma of the Gastro-Esophageal Junction. Proposal of a Specific Staging System. Ann Surg Oncol 2006; 14:299-305.
21. Shannon K. Method for Linear mRNA Amplification. Volume U.S. Pat. No. 6,132,997 2000.
22. Hughes T R, Mao M, Jones A R, Burchard J, Marton M J, Shannon K W, Lefkowitz S M, Ziman M, Schelter J M, Meyer M R, Kobayashi S, Davis C, Dai H, He Y D, Stephaniants S B, Cavet G, Walker W L, West A, Coffey E, Shoemaker D D, Stoughton R, Blanchard A P, Friend S H, Linsley P S. Expression profiling using microarrays fabricated by an ink-jet oligonucleotide synthesizer. Nat Biotechnol 2001; 19:342-7.
23. Marton M J, DeRisi J L, Bennett H A, Iyer V R, Meyer M R, Roberts C J, Stoughton R, Burchard J, Slade D, Dai H, Bassett D E, Jr., Hartwell L H, Brown P O, Friend S H. Drug target validation and identification of secondary drug target effects using DNA microarrays. Nat Med 1998; 4:1293-301.
24. Metropolis N, Ulam S. The Monte Carlo method. J Am Stat Assoc 1949; 44:335-41.
25. Mantel N, Haenszel W. Statistical aspects of the analysis of data from retrospective studies of disease. Journal of the National Cancer Institute 1959; 22:719-748.

The invention claimed is:

1. An in vitro method for identifying a human subject having a poor prognosis of 5-year survival of oesophageal and/or gastro-oesophageal junctional (GOJ) adenocarcinoma, the method comprising the steps of:
    (a) obtaining a tumor tissue sample from said human subject;
    (b) determining by RT-PCR assay the quantitative expression level of a combination of target genes in said in vitro tumor tissue sample obtained in step (a), wherein the combination of target genes consists of TRIM44, SIRT2, EGFR, and WT1, and the RT-PCR assay utilizes at least one primer selected from the group consisting of SEQ ID NO.1, SEQ ID NO.2, SEQ ID NO.4, SEQ ID NO.5, SEQ ID NO.6, and SEQ ID NO.8;
    (c) comparing the expression level of each target gene in said combination determined in step (b) with a reference standard for each target gene;
    (d) detecting an at least 1.3 fold higher level of expression of TRIM44, SIRT2 or EGFR, or an at least 1.3 fold lower level of expression of WT1 as compared with said reference standards in step (c),
    wherein detecting an at least 1.3 fold higher level of expression of at least one of TRIM44, SIRT2 and EGFR as compared with said reference standards indicates a dysregulated TRIM44, SIRT2 and/or EGFR target gene, and an at least 1.3 fold lower level of expression of WT1 as compared with said reference standard indicates a dysregulated WT1 target gene; and
    (e) identifying said human subject as having a poor prognosis of 5-year survival of oesophageal and/or GOJ adenocarcinoma based on the dysregulation of at least two of said target genes in said combination consisting of TRIM44, SIRT2, EGFR, and WT1 as detected in step (d).

2. The in vitro method according to claim 1, wherein said reference standard is selected from the group consisting of:
    an expression level analysis of a tissue sample from at least one subject that does not have oesophageal and/or GOJ adenocarcinoma that is measured in parallel with the tumor tissue sample for expression of said combination of target genes,
    an expression level value for said combination of target genes previously measured from at least one sample taken from at least one subject that does not have oesophageal and/or GOJ adenocarcinoma, and
    a set of expression level values for said combination of target genes measured over time as a mean.

3. An in vitro assay for identifying a patient with poor prognosis of 5-year survival of oesophageal and/or gastro-oesophageal junctional (GOJ) adenocarcinoma comprising:
    (a) conducting RT-PCR with genetic material from a sample of tumor tissue obtained from said patient to determine a quantitative expression level of a prognostic biomarker panel consisting of biomarkers TRIM44, SIRT2, EGFR, and WT1, wherein the RT-PCR assay utilizes at least one primer selected from the group consisting of SEQ ID NO. 1, SEQ ID NO.2, SEQ ID NO.4, SEQ ID NO.5, SEQ ID NO.6, and SEQ ID NO.8;
    (b) comparing the expression level of said prognostic panel of biomarkers with the expression level of a reference standard of said panel of biomarkers;
    (c) determining an at least 1.3 fold increase in expression level of at least one of TRIM44, SIRT2, and EGFR as compared with said reference standard, optionally determining an at least 1.3 fold decrease in expression level of WT1 as compared with said corresponding reference standard, wherein said determining indicates dysregulation of said biomarker;
    wherein dysregulation of biomarkers TRIM44, SIRT2, EGFR, and/or WT1 identifies the patient as having poor prognosis of 5-year survival of oesophageal and/or GOJ adenocarcinoma; and
    (d) treating the patient for oesophageal and/or GOJ adenocarcinoma with poor prognosis of 5-year survival of oesophageal and/or GOJ adenocarcinoma.

4. The in vitro method according to claim 3, wherein said reference standard is selected from the group consisting of:
    an expression level analysis of genetic material from a sample obtained from at least one subject that does not have oesophageal and/or GOJ adenocarcinoma that is measured in parallel with the tumor tissue sample for expression of said combination of target genes,
    an expression level value for said combination of target genes previously measured in the genetic material from at least one sample taken from at least one subject that does not have oesophageal and/or GOJ adenocarcinoma, and
    a set of expression level values for said combination of target genes measured over time as a mean.

* * * * *

SEQUENCE LISTING

<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: Forward primer for TRIM44

<400> SEQUENCE: 1
tgaggcagaa agtgaatttg ac                                              22

```
<210> SEQ ID NO 2
<211> LENGTH: 20
<212> TYPE: DNA
<213> ORGANISM: Artificial Sequence
<220> FEATURE:
<223> OTHER INFORMATION: Reverse primer for TRIM44

<400> SEQUENCE: 2
ccgagttact ttagggtctg                                                 20

<210> SEQ ID NO 3
<211> LENGTH: 22
<212> TYPE: DNA
<213> ORGANISM: Artificial Sequence
<220> FEATURE:
<223> OTHER INFORMATION: Forward primer for TRIM44

<400> SEQUENCE: 3
tgaggcagaa agtgaatttg ac                                              22

<210> SEQ ID NO 4
<211> LENGTH: 22
<212> TYPE: DNA
<213> ORGANISM: Artificial Sequence
<220> FEATURE:
<223> OTHER INFORMATION: Reverse primer for TRIM44

<400> SEQUENCE: 4
ccgagttact ttagggtctg ag                                              22

<210> SEQ ID NO 5
<211> LENGTH: 20
<212> TYPE: DNA
<213> ORGANISM: Artificial Sequence
<220> FEATURE:
<223> OTHER INFORMATION: Forward primer for SIRT2

<400> SEQUENCE: 5
agtcatctgt ttggtgggag                                                 20

<210> SEQ ID NO 6
<211> LENGTH: 21
<212> TYPE: DNA
<213> ORGANISM: Artificial Sequence
<220> FEATURE:
<223> OTHER INFORMATION: Reverse primer for SIRT2

<400> SEQUENCE: 6
agggtatcta tgttctgcgt g                                               21

<210> SEQ ID NO 7
<211> LENGTH: 20
<212> TYPE: DNA
<213> ORGANISM: Artificial Sequence
<220> FEATURE:
<223> OTHER INFORMATION: Forward primer for SIRT2

<400> SEQUENCE: 7
agtcatctgt ttggtgggag                                                 20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for SIRT2
```

```
<400> SEQUENCE: 8
gggtatctat gttctgcgtg                                              20

<210> SEQ ID NO 9
<211> LENGTH: 21
<212> TYPE: DNA
<213> ORGANISM: Artificial Sequence
<220> FEATURE:
<223> OTHER INFORMATION: Forward primer for DCK

<400> SEQUENCE: 9
ccttccaaac atatgcctgt c                                            21

<210> SEQ ID NO 10
<211> LENGTH: 23
<212> TYPE: DNA
<213> ORGANISM: Artificial Sequence
<220> FEATURE:
<223> OTHER INFORMATION: Reverse primer for DCK

<400> SEQUENCE: 10
tatgtaagca tgtctctgga gtg                                          23

<210> SEQ ID NO 11
<211> LENGTH: 21
<212> TYPE: DNA
<213> ORGANISM: Artificial Sequence
<220> FEATURE:
<223> OTHER INFORMATION: Forward primer for DCK

<400> SEQUENCE: 11
ccttccaaac atatgcctgt c                                            21

<210> SEQ ID NO 12
<211> LENGTH: 21
<212> TYPE: DNA
<213> ORGANISM: Artificial Sequence
<220> FEATURE:
<223> OTHER INFORMATION: Reverse primer for DCK

<400> SEQUENCE: 12
tgtaagcatg tctctggagt g                                            21

<210> SEQ ID NO 13
<211> LENGTH: 21
<212> TYPE: DNA
<213> ORGANISM: Artificial Sequence
<220> FEATURE:
<223> OTHER INFORMATION: Forward primer for PAPSS2

<400> SEQUENCE: 13
aaccattgtt gccatctttc c                                            21

<210> SEQ ID NO 14
<211> LENGTH: 20
<212> TYPE: DNA
<213> ORGANISM: Artificial Sequence
<220> FEATURE:
<223> OTHER INFORMATION: Reverse primer for PAPSS2

<400> SEQUENCE: 14
aaactcattg tgccttgctg                                              20

<210> SEQ ID NO 15
```

```
<211> LENGTH: 20
<212> TYPE: DNA
<213> ORGANISM: Artificial Sequence
<220> FEATURE:
<223> OTHER INFORMATION: Forward primer for PAPSS2

<400> SEQUENCE: 15
accattgttg ccatctttcc                                               20

<210> SEQ ID NO 16
<211> LENGTH: 20
<212> TYPE: DNA
<213> ORGANISM: Artificial Sequence
<220> FEATURE:
<223> OTHER INFORMATION: Reverse primer for PAPSS2

<400> SEQUENCE: 16
aaactcattg tgccttgctg                                               20

<210> SEQ ID NO 17
<211> LENGTH: 344
<212> TYPE: PRT
<213> ORGANISM: Homo sapiens

<400> SEQUENCE: 17
```

Met Ala Ser Gly Val Gly Ala Ala Phe Glu Glu Leu Pro His Asp Gly
1               5                   10                  15

Thr Cys Asp Glu Cys Glu Pro Asp Glu Ala Pro Gly Ala Glu Glu Val
            20                  25                  30

Cys Arg Glu Cys Gly Phe Cys Tyr Cys Arg Arg His Ala Glu Ala His
        35                  40                  45

Arg Gln Lys Phe Leu Ser His His Leu Ala Glu Tyr Val His Gly Ser
    50                  55                  60

Gln Ala Trp Thr Pro Pro Ala Asp Gly Glu Gly Ala Gly Lys Glu Glu
65                  70                  75                  80

Ala Glu Val Lys Val Glu Gln Glu Arg Glu Ile Glu Ser Glu Ala Gly
                85                  90                  95

Glu Glu Ser Glu Ser Glu Glu Glu Ser Glu Ser Glu Glu Ser Glu
            100                 105                 110

Thr Glu Glu Glu Ser Glu Asp Glu Ser Asp Glu Glu Ser Glu Glu Asp
        115                 120                 125

Ser Glu Glu Glu Met Glu Asp Glu Gln Glu Ser Glu Ala Glu Glu Asp
    130                 135                 140

Asn Gln Glu Glu Gly Glu Ser Glu Ala Glu Gly Glu Thr Glu Ala Glu
145                 150                 155                 160

Ser Glu Phe Asp Pro Glu Ile Glu Met Glu Ala Glu Arg Val Ala Lys
                165                 170                 175

Arg Lys Cys Pro Asp His Gly Leu Asp Leu Ser Thr Tyr Cys Gln Glu
            180                 185                 190

Asp Arg Gln Leu Ile Cys Val Leu Cys Pro Val Ile Gly Ala His Gln
        195                 200                 205

Gly His Gln Leu Ser Thr Leu Asp Glu Ala Phe Glu Glu Leu Arg Ser
    210                 215                 220

Lys Asp Ser Gly Gly Leu Lys Ala Ala Met Ile Glu Leu Val Glu Arg
225                 230                 235                 240

Leu Lys Phe Lys Ser Ser Asp Pro Lys Val Thr Arg Asp Gln Met Lys
                245                 250                 255

Met Phe Ile Gln Gln Glu Phe Lys Lys Val Gln Lys Val Ile Ala Asp

```
                260                 265                 270
Glu Glu Gln Lys Ala Leu His Leu Val Asp Ile Gln Glu Ala Met Ala
            275                 280                 285

Thr Ala His Val Thr Glu Ile Leu Ala Asp Ile Gln Ser His Met Asp
        290                 295                 300

Arg Leu Met Thr Gln Met Ala Gln Ala Lys Glu Gln Leu Asp Thr Ser
305                 310                 315                 320

Asn Glu Ser Ala Glu Pro Lys Ala Glu Gly Asp Glu Glu Gly Pro Ser
                325                 330                 335

Gly Ala Ser Glu Glu Glu Asp Thr
            340

<210> SEQ ID NO 18
<211> LENGTH: 614
<212> TYPE: PRT
<213> ORGANISM: Homo sapiens

<400> SEQUENCE: 18

Met Ser Gly Ile Lys Lys Gln Lys Thr Glu Asn Gln Gln Lys Ser Thr
1               5                   10                  15

Asn Val Val Tyr Gln Ala His Val Ser Arg Asn Lys Arg Gly Gln
            20                  25                  30

Val Val Gly Thr Arg Gly Gly Phe Arg Gly Cys Thr Val Trp Leu Thr
        35                  40                  45

Gly Leu Ser Gly Ala Gly Lys Thr Thr Ile Ser Phe Ala Leu Glu Glu
    50                  55                  60

Tyr Leu Val Ser His Ala Ile Pro Cys Tyr Ser Leu Asp Gly Asp Asn
65                  70                  75                  80

Val Arg His Gly Leu Asn Arg Asn Leu Gly Phe Ser Pro Gly Asp Arg
                85                  90                  95

Glu Glu Asn Ile Arg Arg Ile Ala Glu Val Ala Lys Leu Phe Ala Asp
            100                 105                 110

Ala Gly Leu Val Cys Ile Thr Ser Phe Ile Ser Pro Phe Ala Lys Asp
        115                 120                 125

Arg Glu Asn Ala Arg Lys Ile His Glu Ser Ala Gly Leu Pro Phe Phe
    130                 135                 140

Glu Ile Phe Val Asp Ala Pro Leu Asn Ile Cys Glu Ser Arg Asp Val
145                 150                 155                 160

Lys Gly Leu Tyr Lys Arg Ala Arg Ala Gly Glu Ile Lys Gly Phe Thr
                165                 170                 175

Gly Ile Asp Ser Asp Tyr Glu Lys Pro Glu Thr Pro Glu Arg Val Leu
            180                 185                 190

Lys Thr Asn Leu Ser Thr Val Ser Asp Cys Val His Gln Val Val Glu
        195                 200                 205

Leu Leu Gln Glu Gln Asn Ile Val Pro Tyr Thr Ile Ile Lys Asp Ile
    210                 215                 220

His Glu Leu Phe Val Pro Glu Asn Lys Leu Asp His Val Arg Ala Glu
225                 230                 235                 240

Ala Glu Thr Leu Pro Ser Leu Ser Ile Thr Lys Leu Asp Leu Gln Trp
                245                 250                 255

Val Gln Val Leu Ser Glu Gly Trp Ala Thr Pro Leu Lys Gly Phe Met
            260                 265                 270

Arg Glu Lys Glu Tyr Leu Gln Val Met His Phe Asp Thr Leu Leu Asp
        275                 280                 285
```

```
Asp Gly Val Ile Asn Met Ser Ile Pro Ile Val Leu Pro Val Ser Ala
            290                 295                 300

Glu Asp Lys Thr Arg Leu Glu Gly Cys Ser Lys Phe Val Leu Ala His
305                 310                 315                 320

Gly Gly Arg Arg Val Ala Ile Leu Arg Asp Ala Glu Phe Tyr Glu His
                325                 330                 335

Arg Lys Glu Glu Arg Cys Ser Arg Val Trp Gly Thr Thr Cys Thr Lys
            340                 345                 350

His Pro His Ile Lys Met Val Met Glu Ser Gly Asp Trp Leu Val Gly
            355                 360                 365

Gly Asp Leu Gln Val Leu Glu Lys Ile Arg Trp Asn Asp Gly Leu Asp
370                 375                 380

Gln Tyr Arg Leu Thr Pro Leu Glu Leu Lys Gln Lys Cys Lys Glu Met
385                 390                 395                 400

Asn Ala Asp Ala Val Phe Ala Phe Gln Leu Arg Asn Pro Val His Asn
                405                 410                 415

Gly His Ala Leu Leu Met Gln Asp Thr Arg Arg Arg Leu Leu Glu Arg
            420                 425                 430

Gly Tyr Lys His Pro Val Leu Leu Leu His Pro Leu Gly Gly Trp Thr
            435                 440                 445

Lys Asp Asp Asp Val Pro Leu Asp Trp Arg Met Lys Gln His Ala Ala
450                 455                 460

Val Leu Glu Glu Gly Val Leu Asp Pro Lys Ser Thr Ile Val Ala Ile
465                 470                 475                 480

Phe Pro Ser Pro Met Leu Tyr Ala Gly Pro Thr Glu Val Gln Trp His
                485                 490                 495

Cys Arg Ser Arg Met Ile Ala Gly Ala Asn Phe Tyr Ile Val Gly Arg
            500                 505                 510

Asp Pro Ala Gly Met Pro His Pro Glu Thr Lys Lys Asp Leu Tyr Glu
            515                 520                 525

Pro Thr His Gly Gly Lys Val Leu Ser Met Ala Pro Gly Leu Thr Ser
            530                 535                 540

Val Glu Ile Ile Pro Phe Arg Val Ala Ala Tyr Asn Lys Ala Lys Lys
545                 550                 555                 560

Ala Met Asp Phe Tyr Asp Pro Ala Arg His Asn Glu Phe Asp Phe Ile
                565                 570                 575

Ser Gly Thr Arg Met Arg Lys Leu Ala Arg Glu Gly Glu Asn Pro Pro
            580                 585                 590

Asp Gly Phe Met Ala Pro Lys Ala Trp Lys Val Leu Thr Asp Tyr Tyr
            595                 600                 605

Arg Ser Leu Glu Lys Asn
    610

<210> SEQ ID NO 19
<211> LENGTH: 389
<212> TYPE: PRT
<213> ORGANISM: Homo sapiens

<400> SEQUENCE: 19

Met Ala Glu Pro Asp Pro Ser His Pro Leu Glu Thr Gln Ala Gly Lys
1               5                   10                  15

Val Gln Glu Ala Gln Asp Ser Asp Ser Asp Ser Glu Gly Gly Ala Ala
            20                  25                  30

Gly Gly Glu Ala Asp Met Asp Phe Leu Arg Asn Leu Phe Ser Gln Thr
        35                  40                  45
```

Leu Ser Leu Gly Ser Gln Lys Glu Arg Leu Leu Asp Glu Leu Thr Leu
 50                  55                  60

Glu Gly Val Ala Arg Tyr Met Gln Ser Glu Arg Cys Arg Val Ile
 65                  70                  75                  80

Cys Leu Val Gly Ala Gly Ile Ser Thr Ser Ala Gly Ile Pro Asp Phe
                     85                  90                  95

Arg Ser Pro Ser Thr Gly Leu Tyr Asp Asn Leu Glu Lys Tyr His Leu
                100                 105                 110

Pro Tyr Pro Glu Ala Ile Phe Glu Ile Ser Tyr Phe Lys Lys His Pro
            115                 120                 125

Glu Pro Phe Phe Ala Leu Ala Lys Glu Leu Tyr Pro Gly Gln Phe Lys
130                 135                 140

Pro Thr Ile Cys His Tyr Phe Met Arg Leu Leu Lys Asp Lys Gly Leu
145                 150                 155                 160

Leu Leu Arg Cys Tyr Thr Gln Asn Ile Asp Thr Leu Glu Arg Ile Ala
                165                 170                 175

Gly Leu Glu Gln Glu Asp Leu Val Glu Ala His Gly Thr Phe Tyr Thr
            180                 185                 190

Ser His Cys Val Ser Ala Ser Cys Arg His Glu Tyr Pro Leu Ser Trp
    195                 200                 205

Met Lys Glu Lys Ile Phe Ser Glu Val Thr Pro Lys Cys Glu Asp Cys
210                 215                 220

Gln Ser Leu Val Lys Pro Asp Ile Val Phe Phe Gly Glu Ser Leu Pro
225                 230                 235                 240

Ala Arg Phe Phe Ser Cys Met Gln Ser Asp Phe Leu Lys Val Asp Leu
                245                 250                 255

Leu Leu Val Met Gly Thr Ser Leu Gln Val Gln Pro Phe Ala Ser Leu
            260                 265                 270

Ile Ser Lys Ala Pro Leu Ser Thr Pro Arg Leu Leu Ile Asn Lys Glu
        275                 280                 285

Lys Ala Gly Gln Ser Asp Pro Phe Leu Gly Met Ile Met Gly Leu Gly
    290                 295                 300

Gly Gly Met Asp Phe Asp Ser Lys Lys Ala Tyr Arg Asp Val Ala Trp
305                 310                 315                 320

Leu Gly Glu Cys Asp Gln Gly Cys Leu Ala Leu Ala Glu Leu Leu Gly
                325                 330                 335

Trp Lys Lys Glu Leu Glu Asp Leu Val Arg Arg Glu His Ala Ser Ile
            340                 345                 350

Asp Ala Gln Ser Gly Ala Gly Val Pro Asn Pro Ser Thr Ser Ala Ser
        355                 360                 365

Pro Lys Lys Ser Pro Pro Ala Lys Asp Glu Ala Arg Thr Thr Glu
    370                 375                 380

Arg Glu Lys Pro Gln
385

<210> SEQ ID NO 20
<211> LENGTH: 260
<212> TYPE: PRT
<213> ORGANISM: Homo sapiens

<400> SEQUENCE: 20

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala

```
            20                  25                  30
Gly Lys Ser Thr Phe Val Asn Ile Leu Lys Gln Leu Cys Glu Asp Trp
            35                  40                  45

Glu Val Val Pro Glu Pro Val Ala Arg Trp Cys Asn Val Gln Ser Thr
        50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Arg Ile Arg Ala Gln Leu Ala Ser Leu
            100                 105                 110

Asn Gly Lys Leu Lys Asp Ala Glu Lys Pro Val Leu Phe Phe Glu Arg
            115                 120                 125

Ser Val Tyr Ser Asp Arg Tyr Ile Phe Ala Ser Asn Leu Tyr Glu Ser
            130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
            195                 200                 205

His Tyr Lys His Glu Ser Trp Leu Leu His Arg Thr Leu Lys Thr Asn
            210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 21
<211> LENGTH: 497
<212> TYPE: PRT
<213> ORGANISM: Homo sapiens

<400> SEQUENCE: 21

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
            35                  40                  45

Ser Ala Glu Arg Leu Gln Gly Arg Arg Ser Arg Gly Ala Ser Gly Ser
            50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
            115                 120                 125
```

```
Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
                195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Val Tyr Gly Cys His Thr
            260                 265                 270

Pro Thr Asp Ser Cys Thr Gly Ser Gln Ala Leu Leu Leu Arg Thr Pro
            275                 280                 285

Tyr Ser Ser Asp Asn Leu Tyr Gln Met Thr Ser Gln Leu Glu Cys Met
290                 295                 300

Thr Trp Asn Gln Met Asn Leu Gly Ala Thr Leu Lys Gly His Ser Thr
305                 310                 315                 320

Gly Tyr Glu Ser Asp Asn His Thr Thr Pro Ile Leu Cys Gly Ala Gln
                325                 330                 335

Tyr Arg Ile His Thr His Gly Val Phe Arg Gly Ile Gln Asp Val Arg
            340                 345                 350

Arg Val Pro Gly Val Ala Pro Thr Leu Val Arg Ser Ala Ser Glu Thr
            355                 360                 365

Ser Glu Lys Arg Pro Phe Met Cys Ala Tyr Pro Gly Cys Asn Lys Arg
    370                 375                 380

Tyr Phe Lys Leu Ser His Leu Gln Met His Ser Arg Lys His Thr Gly
385                 390                 395                 400

Glu Lys Pro Tyr Gln Cys Asp Phe Lys Asp Cys Glu Arg Arg Phe Ser
                405                 410                 415

Arg Ser Asp Gln Leu Lys Arg His Gln Arg Arg His Thr Gly Val Lys
            420                 425                 430

Pro Phe Gln Cys Lys Thr Cys Gln Arg Lys Phe Ser Arg Ser Asp His
            435                 440                 445

Leu Lys Thr His Thr Arg Thr His Thr Gly Glu Lys Pro Phe Ser Cys
    450                 455                 460

Arg Trp Pro Ser Cys Gln Lys Lys Phe Ala Arg Ser Asp Glu Leu Val
465                 470                 475                 480

Arg His His Asn Met His Gln Arg Asn Met Thr Lys Leu Gln Leu Ala
                485                 490                 495

Leu

<210> SEQ ID NO 22
<211> LENGTH: 1210
<212> TYPE: PRT
<213> ORGANISM: Homo sapiens

<400> SEQUENCE: 22
```

-continued

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
            130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
            210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
```

```
            420              425              430
His Gly Gln Phe Ser Leu Ala Val Val Ser Leu Asn Ile Thr Ser Leu
                435              440              445
Gly Leu Arg Ser Leu Lys Glu Ile Ser Asp Gly Asp Val Ile Ile Ser
450              455              460
Gly Asn Lys Asn Leu Cys Tyr Ala Asn Thr Ile Asn Trp Lys Lys Leu
465              470              475              480
Phe Gly Thr Ser Gly Gln Lys Thr Lys Ile Ile Ser Asn Arg Gly Glu
                485              490              495
Asn Ser Cys Lys Ala Thr Gly Gln Val Cys His Ala Leu Cys Ser Pro
            500              505              510
Glu Gly Cys Trp Gly Pro Glu Pro Arg Asp Cys Val Ser Cys Arg Asn
            515              520              525
Val Ser Arg Gly Arg Glu Cys Val Asp Lys Cys Asn Leu Leu Glu Gly
            530              535              540
Glu Pro Arg Glu Phe Val Glu Asn Ser Glu Cys Ile Gln Cys His Pro
545              550              555              560
Glu Cys Leu Pro Gln Ala Met Asn Ile Thr Cys Thr Gly Arg Gly Pro
                565              570              575
Asp Asn Cys Ile Gln Cys Ala His Tyr Ile Asp Gly Pro His Cys Val
            580              585              590
Lys Thr Cys Pro Ala Gly Val Met Gly Glu Asn Asn Thr Leu Val Trp
            595              600              605
Lys Tyr Ala Asp Ala Gly His Val Cys His Leu Cys His Pro Asn Cys
            610              615              620
Thr Tyr Gly Cys Thr Gly Pro Gly Leu Glu Gly Cys Pro Thr Asn Gly
625              630              635              640
Pro Lys Ile Pro Ser Ile Ala Thr Gly Met Val Gly Ala Leu Leu Leu
                645              650              655
Leu Leu Val Val Ala Leu Gly Ile Gly Leu Phe Met Arg Arg Arg His
            660              665              670
Ile Val Arg Lys Arg Thr Leu Arg Arg Leu Leu Gln Glu Arg Glu Leu
            675              680              685
Val Glu Pro Leu Thr Pro Ser Gly Glu Ala Pro Asn Gln Ala Leu Leu
            690              695              700
Arg Ile Leu Lys Glu Thr Glu Phe Lys Lys Ile Lys Val Leu Gly Ser
705              710              715              720
Gly Ala Phe Gly Thr Val Tyr Lys Gly Leu Trp Ile Pro Glu Gly Glu
                725              730              735
Lys Val Lys Ile Pro Val Ala Ile Lys Glu Leu Arg Glu Ala Thr Ser
            740              745              750
Pro Lys Ala Asn Lys Glu Ile Leu Asp Glu Ala Tyr Val Met Ala Ser
            755              760              765
Val Asp Asn Pro His Val Cys Arg Leu Leu Gly Ile Cys Leu Thr Ser
            770              775              780
Thr Val Gln Leu Ile Thr Gln Leu Met Pro Phe Gly Cys Leu Leu Asp
785              790              795              800
Tyr Val Arg Glu His Lys Asp Asn Ile Gly Ser Gln Tyr Leu Leu Asn
                805              810              815
Trp Cys Val Gln Ile Ala Lys Gly Met Asn Tyr Leu Glu Asp Arg Arg
            820              825              830
Leu Val His Arg Asp Leu Ala Ala Arg Asn Val Leu Val Lys Thr Pro
            835              840              845
```

Gln His Val Lys Ile Thr Asp Phe Gly Leu Ala Lys Leu Leu Gly Ala
    850                 855                 860

Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 23
<211> LENGTH: 216
<212> TYPE: PRT
<213> ORGANISM: Homo sapiens

<400> SEQUENCE: 23

```
Met Pro Glu Gly Pro Leu Val Arg Lys Phe His His Leu Val Ser Pro
1               5                   10                  15

Phe Val Gly Gln Gln Val Val Lys Thr Gly Gly Ser Ser Lys Lys Leu
            20                  25                  30

Gln Pro Ala Ser Leu Gln Ser Leu Trp Leu Gln Asp Thr Gln Val Arg
        35                  40                  45

Leu Val Leu His Phe Gly Gly Gly Phe Leu Ala Phe Tyr Asn Cys
    50                  55                  60

Gln Leu Ser Trp Ser Ser Pro Val Thr Pro Thr Cys Asp Ile
65                  70                  75                  80

Leu Ser Glu Lys Phe His Arg Gly Gln Ala Leu Glu Ala Leu Gly Gln
                85                  90                  95

Ala Gln Pro Val Cys Tyr Thr Leu Leu Asp Gln Arg Tyr Phe Ser Gly
            100                 105                 110

Leu Gly Asn Ile Ile Lys Asn Glu Ala Leu Tyr Arg Ala Gly Ile His
        115                 120                 125

Pro Leu Ser Leu Gly Ser Val Leu Ser Ala Ser Arg Arg Glu Val Leu
    130                 135                 140

Val Asp His Val Val Glu Phe Ser Thr Ala Trp Leu Gln Gly Lys Phe
145                 150                 155                 160

Gln Gly Arg Pro Gln His Thr Gln Val Tyr Gln Lys Glu Gln Cys Pro
                165                 170                 175

Ala Gly His Gln Val Met Lys Glu Ala Phe Gly Pro Glu Asp Gly Leu
            180                 185                 190

Gln Arg Leu Thr Trp Trp Cys Pro Gln Cys Gln Pro Gln Leu Ser Glu
        195                 200                 205

Glu Pro Glu Gln Cys Gln Phe Ser
    210                 215
```

<210> SEQ ID NO 24
<211> LENGTH: 549
<212> TYPE: PRT
<213> ORGANISM: Homo sapiens

<400> SEQUENCE: 24

```
Met Glu Phe Ala Glu Leu Ile Lys Thr Pro Arg Val Asp Asn Val Val
1               5                   10                  15

Leu His Arg Pro Phe Tyr Pro Ala Val Glu Gly Thr Leu Cys Leu Thr
            20                  25                  30

Gly His His Leu Ile Leu Ser Ser Arg Gln Asp Asn Thr Glu Glu Leu
        35                  40                  45

Trp Leu Leu His Ser Asn Ile Asp Ala Ile Asp Lys Arg Phe Val Gly
    50                  55                  60

Ser Leu Gly Thr Ile Ile Ile Lys Cys Lys Asp Phe Arg Ile Ile Gln
65                  70                  75                  80

Leu Asp Ile Pro Gly Met Glu Glu Cys Leu Asn Ile Ala Ser Ser Ile
                85                  90                  95

Glu Ala Leu Ser Thr Leu Asp Ser Ile Thr Leu Met Tyr Pro Phe Phe
            100                 105                 110

Tyr Arg Pro Met Phe Glu Val Ile Glu Asp Gly Trp His Ser Phe Leu
        115                 120                 125

Pro Glu Gln Glu Phe Glu Leu Tyr Ser Ser Ala Thr Ser Glu Trp Arg
    130                 135                 140
```

```
Leu Ser Tyr Val Asn Lys Glu Phe Ala Val Cys Pro Ser Tyr Pro Pro
145                 150                 155                 160

Ile Val Thr Val Pro Lys Ser Ile Asp Asp Glu Ala Leu Arg Lys Val
                165                 170                 175

Ala Thr Phe Arg His Gly Gly Arg Phe Pro Val Leu Ser Tyr Tyr His
            180                 185                 190

Lys Lys Asn Gly Met Val Ile Met Arg Ser Gly Gln Pro Leu Thr Gly
        195                 200                 205

Thr Asn Gly Arg Arg Cys Lys Glu Asp Glu Lys Leu Ile Asn Ala Thr
    210                 215                 220

Leu Arg Ala Gly Lys Arg Gly Tyr Ile Ile Asp Thr Arg Ser Leu Asn
225                 230                 235                 240

Val Ala Gln Gln Thr Arg Ala Lys Gly Gly Phe Glu Gln Glu Ala
                245                 250                 255

His Tyr Pro Gln Trp Arg Arg Ile His Lys Ser Ile Glu Arg Tyr His
            260                 265                 270

Ile Leu Gln Glu Ser Leu Ile Lys Leu Val Glu Ala Cys Asn Asp Gln
        275                 280                 285

Thr His Asn Met Asp Arg Trp Leu Ser Lys Leu Glu Ala Ser Asn Trp
    290                 295                 300

Leu Thr His Ile Lys Glu Ile Leu Thr Thr Ala Cys Leu Ala Ala Gln
305                 310                 315                 320

Cys Ile Asp Arg Glu Gly Ala Ser Ile Leu Ile His Gly Thr Glu Gly
                325                 330                 335

Thr Asp Ser Thr Leu Gln Val Thr Ser Leu Ala Gln Ile Ile Leu Glu
            340                 345                 350

Pro Arg Ser Arg Thr Ile Arg Gly Phe Glu Ala Leu Ile Glu Arg Glu
        355                 360                 365

Trp Leu Gln Ala Gly His Pro Phe Gln Gln Arg Cys Ala Gln Ser Ala
    370                 375                 380

Tyr Cys Asn Thr Lys Gln Lys Trp Glu Ala Pro Val Phe Leu Leu Phe
385                 390                 395                 400

Leu Asp Cys Val Trp Gln Ile Leu Arg Gln Phe Pro Cys Ser Phe Glu
                405                 410                 415

Phe Asn Glu Asn Phe Leu Ile Met Leu Phe Glu His Ala Tyr Ala Ser
            420                 425                 430

Gln Phe Gly Thr Phe Leu Gly Asn Asn Glu Ser Glu Arg Cys Lys Leu
        435                 440                 445

Lys Leu Gln Gln Lys Thr Met Ser Leu Trp Ser Trp Val Asn Gln Pro
450                 455                 460

Ser Glu Leu Ser Lys Phe Thr Asn Pro Leu Phe Glu Ala Asn Asn Leu
465                 470                 475                 480

Val Ile Trp Pro Ser Val Ala Pro Gln Ser Leu Pro Leu Trp Glu Gly
                485                 490                 495

Ile Phe Leu Arg Trp Asn Arg Ser Ser Lys Tyr Leu Asp Glu Ala Tyr
            500                 505                 510

Glu Glu Met Val Asn Ile Ile Glu Tyr Asn Lys Glu Leu Gln Ala Lys
        515                 520                 525

Val Asn Ile Leu Arg Arg Gln Leu Ala Glu Leu Glu Thr Glu Asp Gly
    530                 535                 540

Met Gln Glu Ser Pro
545
```